US012779238B2

(12) United States Patent
Wang et al.

(10) Patent No.: US 12,779,238 B2
(45) Date of Patent: Nov. 3, 2026

(54) SPINTRONIC NANODEVICE FOR LOW-POWER, CELLULAR-LEVEL, MAGNETIC NEUROSTIMULATION

(71) Applicant: Regents of the University of Minnesota, Minneapolis, MN (US)

(72) Inventors: Jian-Ping Wang, Minneapolis, MN (US); Renata Saha, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1029 days.

(21) Appl. No.: 17/995,237

(22) PCT Filed: Apr. 1, 2021

(86) PCT No.: PCT/US2021/025313
§ 371 (c)(1),
(2) Date: Sep. 30, 2022

(87) PCT Pub. No.: WO2021/202834
PCT Pub. Date: Oct. 7, 2021

(65) Prior Publication Data

US 2023/0149729 A1 May 18, 2023

Related U.S. Application Data

(60) Provisional application No. 63/004,857, filed on Apr. 3, 2020.

(51) Int. Cl.
*A61N 2/00* (2006.01)
*H01F 10/32* (2006.01)

(52) U.S. Cl.
CPC ......... *A61N 2/006* (2013.01); *H01F 10/3286* (2013.01)

(58) Field of Classification Search
CPC ... A61N 2/006; H01F 10/3286; H01F 10/325; H01F 10/3236; B82Y 25/00
(Continued)

(56) References Cited

U.S. PATENT DOCUMENTS

| | | | |
|---|---|---|---|
| 6,280,376 | B1 | 8/2001 | Holcomb |
| 6,678,562 | B1 | 1/2004 | Tepper et al. |

(Continued)

FOREIGN PATENT DOCUMENTS

| | | | |
|---|---|---|---|
| CN | 204121602 | U | 1/2015 |
| WO | 2015153868 | A1 | 10/2015 |

(Continued)

OTHER PUBLICATIONS

Roth et al., The magnetic field of a single axon, Journal of Biophysical Society, vol. 48, pp. 93-109, 1985.

(Continued)

*Primary Examiner* — Sunita Reddy
(74) *Attorney, Agent, or Firm* — Theodore M. Magee; Westman, Champlin & Koehler, P.A.

(57) ABSTRACT

A neuro-stimulation system includes a stimulator controller, a support surface, and a magneto-ionic stimulator positioned on the support surface and electrically connected to the stimulator controller. The stimulator controller can apply a voltage to the magneto-ionic stimulator, wherein a change in the voltage causes a change in a magnetic field produced by the magneto-ionic stimulator.

4 Claims, 16 Drawing Sheets

(58) Field of Classification Search
USPC .......................................................... 600/9–15
See application file for complete search history.

(56) References Cited

U.S. PATENT DOCUMENTS

| | | | | |
|---|---|---|---|---|
| 9,999,781 | B2 | 6/2018 | Gale et al. | |
| 10,201,715 | B2 | 2/2019 | Wang et al. | |
| 10,213,615 | B2 | 2/2019 | Gale et al. | |
| 2004/0006264 | A1 | 1/2004 | Mojarradi et al. | |
| 2005/0275497 | A1 | 12/2005 | Ramadan et al. | |
| 2006/0212097 | A1 | 9/2006 | Varadan et al. | |
| 2007/0067004 | A1 | 3/2007 | Boveja et al. | |
| 2009/0157151 | A1 | 6/2009 | Cauller et al. | |
| 2009/0248098 | A1 | 10/2009 | Penny et al. | |
| 2010/0324642 | A1 | 12/2010 | Pettinelli | |
| 2012/0078327 | A1* | 3/2012 | Sloan | A61B 5/4064 607/72 |
| 2014/0081073 | A1 | 3/2014 | Nishi et al. | |
| 2014/0163305 | A1 | 6/2014 | Watterson | |
| 2016/0303392 | A1 | 10/2016 | Wang et al. | |
| 2017/0001003 | A1* | 1/2017 | Pivonka | A61N 1/36067 |
| 2017/0225004 | A1* | 8/2017 | Casse | A61N 2/02 |
| 2018/0133460 | A1 | 5/2018 | Townley et al. | |
| 2019/0099609 | A1* | 4/2019 | Lee | A61N 2/006 |
| 2019/0172998 | A1* | 6/2019 | Tan | C25B 1/04 |
| 2019/0231264 | A1 | 8/2019 | Higbie et al. | |
| 2020/0306539 | A1 | 10/2020 | Kim et al. | |
| 2021/0299656 | A1 | 9/2021 | Malic et al. | |
| 2022/0176141 | A1 | 6/2022 | Caparso et al. | |
| 2022/0362570 | A1* | 11/2022 | Pemberton | A61N 2/02 |
| 2023/0173293 | A1 | 6/2023 | Wang et al. | |

FOREIGN PATENT DOCUMENTS

| | | | |
|---|---|---|---|
| WO | 2018227165 | A1 | 12/2018 |
| WO | 2019100055 | A1 | 5/2019 |
| WO | 2021202840 | A1 | 10/2021 |
| WO | 2023025939 | A1 | 3/2023 |
| WO | 2025049951 | A1 | 3/2025 |

OTHER PUBLICATIONS

Rousche et al., Flexible polyimide-based intracortical electrode arrays with bioactive capability, IEEE Transactions on Biomedical Engineering, vol. 48, No. 3, pp. 361-371, 2001.

Roy et al., Biomedical applications of diamond-like carbon coatings: a review, Wiley, Interscience, pp. 72-84, 2006.

Rubehn et al., A MEMS-based flexible multichannel ECoG-electrode array, Journal of Neural Engineering, vol. 6, 10 pages, 2009.

Saha, Tunable magnetic skyrmions in spintronic nanostructures for cellular-level magnetic neurostimulation, Journal of Physics D: Applied Physics, vol. 52, 11 pages, 2019.

Saltzberg et al., Pharmacological characterization of P2Y receptor subtypes on isolated tiger salamander muller cells, GLIA, vol. 42, pp. 149-159, 2003.

Shinwari et al., Microfabricated reference electrodes and their biosensing applications, Sensors, vol. 10, pp. 1679-1715, 2010.

Srinivasan et al., A detection system based on giant magnetoresistive sensors and high-moment magnetic nanoparticles demonstrates zeptomole sensitivity: potential for personalized medicine, Communications, Biosensors, Angew, Chem. Int. Ed., vol. 48, pp. 2764-2767, 2009.

Su et al., Tunable magnetic domain walls for therapeutic neuromodulation at cellular level: stimulating neurons through magnetic nanowires, Journal of Applied Physics, vol. 126, 14, pages, 2019.

Suh et al., Neurovascular coupling and oximetry during epileptic events, Molecular Neurobiology, vol. 33, pp. 181-197, 2006.

Tan et al., Magneto-ionic control of magnetisum using a solid-state proton pump, Nature Materials, vol. 18, pp. 35-42, 2019.

Tanghe et al., A 16-channel CMOS neural stimulating array, IEEE Journal of Solid-State Circuits, vol. 27, No. 12, pp. 1819-1825, 1992.

Tetienne et al., Nitrogen-vacancy-center imaging of bubble domains in a 6-A film of cobalt with perpendicular magnetization, Journal of Applied Physics, vol. 115, pp. 17D501-1-17D501-3, 2014.

Triarhou et al., Transplantation of ventral mesencephalic analgen to a genetic model of nigrostriatal dopamine deficiency, Proceedings of the National Academy of Science, vol. 83, pp. 8789-8793, 1986.

Van der Wel, MOSFET 1/f noise measurement under switched bias condictidons, IEEE Electron Device Letters, vol. 21, No. 1, pp. 43-46, 2000.

Viventi et al., Flexible foldable actively multiplexed, high-density electrode array for mapping brain activity in vivo, Nature Neuroscience, Technical Reports, vol. 14, No. 12, pp. 1599-1607, 2011.

Weiland et al., In vitro electrical properties for iridium oxide versus titanium nitride stimulating electrodes, IEEE Transactions on Biomedical Engineering, vol. 49, No. 12, pp. 1574-1579, 2022.

West et al., A simple model for calculating magnetic nano-wire domain wall fringing fields, Journal of Physics D: Applied Physics, vol. 45, pp. 1-9, 2012.

Wikipedia, https://en.wikipedia.org/wiki/neurostimulation, 2016.

Winkin et al., Flexible multi-electrode array with integrated bendable CMOS-chip for implantable systems, 34th Annual International Conference of the IEEE EMBS, pp. 3882-3885, 2012.

Wise et al., Microfabrication techniques for integrated sensors and microsystems, Science, pp. 1335-1342, 1991.

Wise et al., An integrated-circuit approach to extracellular microelectrodes, IEEE Transactions on Bio-Medical Engineering, vol. BME-17, No. 2, pp. 238-247, 1970.

Wise et al., Wireless implantable microsystems: high-density electronic interfaces to the nervous system, Proceedings of the IEEE, vol. 92, No. 1, pp. 76-97, 2004.

Woosley et al., The magnetic field of a single axon: a volume conductor model, Mathematical Biosciences, vol. 76, pp. 1-36, 1985.

Wu et al., Spin-oribt torque and spin hall effect-based cellular level therapeutic spintronic neuromodulator: a simulation study, The Journal of Physical Chemistry, vol. 123, pp. 24963-24972, 2019.

Amaral et al., Towards a system to measure action potential on mice brain slice with local magneto resistive probes, Journal of Applied Physics 109, 07B308, 14 pages, 2011.

Banks, Neurotechnology, Engineering Science and Education Journal, pp. 135-144, 1998.

Barach et al., Magnetic Measurements of Action Currents in a Single Nerve Axon: A Core-Conductor Model, IEEE Transactions on Biomedical Engineering, vol. BME-32, No. 2, pp. 136-140, 1985.

Bartorelli et al., Aspirin Alone Antiplatelet Regimen After Intracoronary Placement of the Carbostent, Catheterization and Cardiovascular Interventions, vol. 55, pp. 150-156, 2002.

Berger, Motion of a magnetic domain wall traversed by fast-rising current pulses, Journal of Applied Physics, vol. 71, No. 6, pp. 2721-2726, 1992.

Bhowmik et al., Deterministic domain wall motion orthogonal to current flow due to spin orbit torque, Scientific Reports, 10 pages, 2015.

Bloom et al., 1/f noise reduction of metal oxide semiconductor transistors by cycling from inversion to accumulation, Applied Physics Letters, vol. 58, No. 15, pp. 1664-1666, 1991.

Bohning, Mapping transcranial magnetic stimulation (TMS) fields in vivo with MRI, Neuro Report, vol. 8, pp. 2535-2538, 1997.

Bonmassar et al., Microscopic magnetic stimulation of neural tissue, Nature Communications, vol. 3, No. 921, Article, 10 pages, 2012.

Burmeister et al., Glutaraldehyde cross-linked glutamate oxidase coated microelectrode arrays: selectivity and resting levels of glutamate in the CNS, ACS Chemical Neuroscience, vol. 4, pp. 721-728, 2013.

Cardoso et al., Magnetic tunnel junction sensors with pTesla sensitivity, Microsystem Technology, 11 pages, 2013.

Chaves et al., MgO based picotesla field sensors, Journal of Applied Physics, vol. 103, pp. 07E931-1-07E931-3, 2008.

(56) References Cited

OTHER PUBLICATIONS

Chen et al., Direct electrochemical oxidation of NADPH at a low potential on the carbon nanotube modified glassy carbon electrode, Chinese Journal of Chemistry, vol. 22, No. 2, pp. 167-171, 2004.
Chen et al., Wireless magnetothermal deep brain stimulation, Research, Neurotechniques, vol. 347, No. 6229, pp. 1477-1480, 2015.
Cheung, Implantable microscale neural interfaes, Biomed Microdevices, vol. 9, pp. 923-938, 2007.
Clark et al., A mathematical evaluation of the core conductor model, Biophysical Journal, vol. 6, pp. 95-112, 1966.
Cogan, Neural stimulation and recording electrodes, Annual Review of Biomedical Engineering, vol. 10, pp. 275-309, 2008.
Cogan et al., Sputtered iridium oxide films (SIROFs) for low-impedance neural stimulation and recording electrodes, Proceedings of the 26th Annual International Conference on the IEEE EMBS, pp. 4153-4156, 2004.
Cohen, Magnetoencephalography: Evidence of Magnetic Fields Produced by Alpha-Rhythm Currents, Science, vol. 161, pp. 784-786, 1968.
Dey et al., Nanomaterial-based functional scaffolds for amperometric sensing of bioanalytes, Anal Bioanal Chemical, vol. 405, pp. 3431-3448, 2013.
Dhanapal et al., Reversibly controlled magnetic domains of Co film via electric field driven oxygen migration at nanoscale, Applied Physics Letter, vol. 114, No. 23, 7 pages, 2019.
Di et al., Influence of controlled surface oxidation on the magnetic anisotropy of Co ultrathin films, Applied Physics Letter, vol. 106, 5 pages, 2015.
Dichter, Rat cortical neurons in cell cultrue: culture methods, cell morphology, electrophysiology, and synapse formation, Brain Research, vol. 149, pp. 279-293, 1978.
Dierickx et al., The decrease of "random telegraph signal" noise in metal-oxide semiconductor field-effect transistors when cycled from inversion to accumulation, Journal of Applied Physics, vol. 71, No. 4, pp. 2028-2029, 1993.
Duan et al., Tauroursodeoxycholic acide improves the survival and function of nigral transplants in a rat model of Parkinson's disease, Cell Transplantation, vol. 11, pp. 195-205, 2002.
Lyle et al., Direct communication between magnetic tunnel junctions for nonvolatile logic fan-out architecture, Applied Physics Letters, vol. 97, pp. 152504-1-152504-3, 2010.
Malmivuo, Comparison of the properties of EEG and MEG in detecting the electric activity of the brain, Brain Topogr, vol. 25, pp. 1-19, 2012.
Malmivuo, Bioelectromagnetism: Principles and Applications of Bioelectric and BioMagnetic Fields, Oxford University Press, Part 1, pp. 1-129, 1995.
Malmivuo, Bioelectromagnetism: Principles and Applications of Bioelectric and BioMagnetic Fields, Oxford University Press, Part 2, pp. 130-257, 1995.
Malmivuo, Bioelectromagnetism: Principles and Applications of Bioelectric and BioMagnetic Fields, Oxford University Press, Part 3, pp. 258-385, 1995.
Malmivuo, Bioelectromagnetism: Principles and Applications of Bioelectric and BioMagnetic Fields, Oxford University Press, Part 4, pp. 386-513, 1995.
Malmivuo, Bioelectromagnetism: Principles and Applications of Bioelectric and BioMagnetic Fields, Oxford University Press, Part 5, pp. 514-641, 1995.
Maynard et al., The Utah intracortical electrode array: a recording structure for potential brain-computer interfaces, Electroencephalography and Clinical Neurophysiology, vol. 102, pp. 228-239, 1997.
Medtronic, http://www.medtronic.com/innovation/smarter-dbs.html##sthash.D7onnDeo.dpuf, accessed 2016.
Metz et al., Flexible polyimide probes with microelectrodes and embedded microfluidic channels for simultaneous drug delivery and multi-channel monitoring of bioelectric activity, Biosensors and Bioelectronics, vol. 19, pp. 1309-1318, 2004.
Minusa et al., A multichannel magnetic stimulation system using submillimeter-sized coils: system developed and experimental application to rodent brain in vivo, Journal of Neural Engineering, vol. 16, 21 pages, 2019.
Normann et al., A neural interface for a cortical vision prosthesis, Vision Research, vol. 39, pp. 2577-2587, 1999.
Ordonez e al., Improved polyimide thin-film electrodes for neural implants, 34th Annual International Conference of the IEEE, pp. 5134-5137, 2012.
Park et al., Activation of the central nervous system induced by micro-magnetic stimulation, Nature Communications, 9 pages, 2013.
Parkin et al., Magnetic domain-wall racetrack memory, Science, vol. 320, pp. 190-194, 2008.
Parkinson, http://www.parkinson.org, accessed 2016.
Pearce et al., Microtechnology, Meet neurobiology, Critical Review, The Royal Society of Chemistry, Lab Chip, vol. 7, pp. 30-40, 2007.
Pong et al., Hysteresis loop collapse for linear response in magnetic-tunnel-junction sensors, Journal of Applied Physics, vol. 105, pp. 07E723-1-07E723-3, 2009.
Pundt et al., Transplantation of human striatal tissue into a rodent model of Huntington's Disease: phenotypic expression of transplanted neurons and host-to-graft innervation, Brain Research Bulletin, vol. 39, No. 1, pp. 23-32, 1996.
Rahman et al., Reduction of switching current density in perpendicular magnetic tunnel junctions by tuning the anisotropy of the CoFeB free layer, Journal of Applied Physics, vol. 11, pp. 07C907-1-07C907-3, 2012.
Ramadan et al., Fabrication of three-dimensional magnetic microdevices with embedded microcoils for magnetic potential concentration, Journal of Microelectromechanical Systems, vol. 15, No. 3, pp. 624-638, 2006.
Reinhoud et al., Analysis of glutamate, GABA, noradrenaline, dopamine, serotonin, and metabolites using microbore UHPLC with electrochemical detection, ACS Chemical Neuroscience, vol. 4, pp. 88-894, 2013.
Riklin et al., Glucose and acetylcholine sensing multilayer enzyme electrodes of controlled enzyme layer thickness, Anal. Chem., vol. 67, pp. 4118-4126, 1995.
Rizou et al., Magnetic stimulation in the microscale: the development of a 6x6 array of microcoils for stimulation of excitable cells in vitro, Biomedical Physics & Engineering Express, 14 pages, 2017.
Romani, Fundamentals of Neuromagnetism, Advances in Biomagnetisum, pp. 33-46, 1989.
Enz et al., Circuit techniques for reducing the effects of op-amp imperfections: autozero, correlated double sampling, and chopper stabilization, Proceedings of the IEEE, vol. 84, No. 11, pp. 1584-1614, 1996.
Fukami et al., Current-induced domain wall motion in perpendicularly magnetized coFeB nanowire, Applied Physics etters, vol. 98, pp. 082504-1-082504-3, 2011.
Golestanirad et al., Solenoidal micromagnetic stimulation enables activation of axons with specific orientation, Frontiers in Physiology, Technology Report, vol. 9, Article 724, 15 pages, 2018.
Grill-Spector et al., Differential processing of objects under various viewing conditions in the human lateral occipital complex, Neuron, vol. 24, pp. 187-203, 1999.
Hajjhassan et al., NeuroMEMS: Neural probe microtechnologies, Sensors, vol. 8, pp. 6704-6726, 2008.
Hamalainen et al., Magnetoencephalography-theory, instrumentation, and applications to noninvasive studies of the working human brain, Reviews of Modern Physics, vol. 65, No. 2, 93 pages, 1993.
Hascup et al., Microelectrode array fabrication and optimization for selection neurochemical detection, Microelectrode Biosensors, Meuromethods, vol. 80, pp. 27-54, 2013.
Hu et al., Opportunities and challenges for magnetoelectric devices, Applied Physics Letters, vol. 7, pp. 080905-1-080905-16, 2019.
Intechopen, http://www.intechopen.com, 1 page, accessed 2016.
Jang et al., Two distinct filopodia populations at the growth cone allow to sense nanotopographical extracellular matrix cues to guide neurite outgrowth, Open Access, Sensing of ECM Nanotopographical Cues by Filopodia, vol. 5, No. 12, 11 pages, 2010.

(56) References Cited

OTHER PUBLICATIONS

Jansen et al., Transplantation of fetal neocortex ameliorates sensorimotor and locomotor deficits following neonatal schemic-hypoxic brain injury in rats, Experimental Neurology, vol. 147, pp. 487-497, 1997.
Kassim et al., Tail current flicker noise reduction in LC VCOs by complementary switched biasing, ICM, pp. 102-105, 2003.
Kegley, Testing the efficiency of vertically aligned gold nanowires on a titanium needle implantable neural electrodes in the Rattus Norvegicus Hipposcampus, University of Arkansas, ScholarWorks@UARK, Electrical Engineering Undergraduate Honors, Theses, 41 pages, 2012.
Kim et al., Electroanalytical eavesdropping on single cell communication, Analytical Chemistry, vol. 83, pp. 7242-7249, 2011.
Kim et al., A low-noise WLAN mixer using switched biasing technique, IEEE Microwave and Wireless Components Letters, vol. 19, No. 10, pp. 650-652, 2009.
Kohlmeier et al., An investigation on technologies to fabricate microcoils for miniaturized actuator systems, Microsystem Technologies, vol. 10, pp. 175-181, 2004.
Lee et al., Polyimide-based intracortical neural implant with improved structural stiffness, Journal of Micromechanics and Microengineering, vol. 14, pp. 32-37, 2004.
Lee et al., Wheatstone bridge giant-magnetoresistance based cell counter, Biosensors and Bioelectronics, vol. 57, pp. 48-53, 2014.
Lee et al., Implantable microcoils for intracortical magnetic stimulation, Science Advances, Research Article, Bioengineering, vol. 2, 14 pages, 2016.
Lind et al., The density difference between tissue and neural probes is a key factor for glial scarring, Scientific Reports, vol. 3, 7 pages, 2013.
Liou, High sensitivity magnetoresistive sensors for both DC and EMI magnetic field mapping, University of Nebraska, SERDP Project MR-1716, 19 pages, 2012.
Lorach et al., Neural stimulation for visual rehabilitation: advances and challenges, Journal of Physiology, pp. 421-431, 2013.
Love et al., Diamond like carbon coatings for potential application in biological implants—a review, Tribology International, vol. 63, pp. 141-150, 2013.
Yamaguchi et al., Real-space observation of current-driven domain wall motion in submicron magnetic wires, Physical Review Letters, vol. 92, No. 7, pp. 077205-1-077205-4, 2004.
Yao et al., Improved current switching symmetry of the magnetic tunneling junction and giant magnetoresistance devices with nano-current-channel structure, Journal of Applied Physics, vol. 115, pp. 07A717-1-07A717-3, 2008.
Yue et al., Magneto-electric nano-particles for non-invasive brain stimulation, Open Access, PLOS One, vol. 7, No. 9, pp. 1-5, 2012.
Zhang et al., High power and low critical current spin torque oscillation from a magnetic tunnel junction with a built-in hard axis polarizer, Applied Physics Letters, vol. 100, pp. 032405-1-032405-4, 2012.
Notification of Transmittal of the International Search Report and the Written Opinion of the International Searching Authority, or the Declaration, International Search Report and Written Opinion dated Jul. 8, 2021 for corresponding International Application No. PCT/US2021/025322, 13 pages.
Notification of Transmittal of the International Search Report and the Written Opinion of the International Searching Authority, or the Declaration, International Search Report and Written Opinion dated Jul. 8, 2021 for corresponding International Application No. PCT/US2021/025313, 11 pages.
Prosecution history of U.S. Appl. No. 17/995,229 including: Notice of Allowance dated May 1, 2026, Amendment dated Mar. 5, 2026, Office Action dated Dec. 8, 2025, 40 pages.
PCT Notification of Transmittal of the International Search Report and the Written Opinion of the International Searching Authority, or the Declaration dated Jan. 15, 2025 for corresponding PCT application Serial No. PCT/US2024/044736, 12 pages.
Angotzi et al., A programmable closed-loop recording and stimulating wireless system for behaving small laboratory animals, Scientific Reports, 4:5963, 2014.
Bloom et al., Portable Arbitrary Pulse Generator for Driving μCoils for Micromagnetic Neurostimulation, bioRxiv preprint doi: https://doi.org./10.1101/2023.06.19.545512, 14 pages, 2026.
Bonmassar et al., MRI-Induced heating of coils for microscopic magnetic stimulation at 1.5 Tesla: An initial study, Frontiers in Human Neuroscience, Brief Research Report, vol. 14, Article 53, 10 pages, 2020.
Chappert et al., The emergence of spin electronics in data storage, Nature Mater 6, https://doi.org/10.1038/nmat2024, 813-823, 2007.
Ho et al., Wireless power transfer to deep-tissue microimplants, PNAS, vol. 11, No. 22, pp. 7974-7979, 2014.
Rolston et al., A low-cost multielectrode system for data acquisition enabling real-time closed-loop processing with rapid recovery from stimulation artifacts, Frontiers in Neuroengineering, Original Research Article, vol. 2, Article 12, 17 pages, 2009.
Saha et al., Impact of anesthesia on micromagnetic stimulation (μMS) of the vagus nerve, Biomedical Physics & Engineering Express, vol. 10, 11 pages, 2024.
Saha et al., Micromagnetic stimulation (μMS) dose-response of the rat sciatic nerve, Journal of Neural Engineering, vol. 20, 16 pages, 2023.
Saha et al., Micromagnetic stimulation (μMS) controls dopamine release: an in vivo study using WINCS Harmoni, Biomedical Physics & Engineering Express, vol. 11, 14 pages, 2025.
Tonini et al., Feasibility study of magnetic sensing for detecting single-neuron action potentials, Annals of Biomedical Science and Engineering, pp. 19-29, 2022.
Wu et al., Giant magnetoresistance biosensors in biomedical applications, ACS Appl Mater Interfaces, 49 pages, 2022.
https://www.youtube.com/watch?v=Wiy_eHdj8kg, 7 pages, retrieve as early as 2026.

* cited by examiner

SPINTRONIC NANODEVICE FOR LOW-POWER, CELLULAR-LEVEL, MAGNETIC NEUROSTIMULATION

CROSS-REFERENCE OF RELATED APPLICATION

This application is a Section 371 National Stage Application of International Application No. PCT/US2021/025313, filed Apr. 1, 2021, which is incorporated by reference in its entirety and published as WO 2021/202834A1 on Oct. 7, 2021 and which claims priority of U.S. Provisional Application No. 63/004,857, filed Apr. 3, 2020.

BACKGROUND

By applying a voltage or a changing magnetic field to a nerve cell, it is possible to cause the nerve cell to "fire" during which the nerve cell depolarizes and then repolarizes.

In external magnetic stimulation, a strong alternating magnetic field is generated external to the body and is directed into the body. Within the body, the time-varying magnetic field induces an electric field that creates a current along the nerve cells that cause the cells to fire.

Such external systems require strong magnetic fields in order to penetrate into the body. However, as the magnetic fields increase in strength, the area affected by the magnetic fields also increases resulting in low resolution stimulus of the nerve cells. As a result, it is difficult to direct the external magnetic field to only a select number of nerve cells.

In implantable magnetic stimulation, a probe is placed in the vicinity of the nerve cells within the body and a magnetic field is generated at the end of the probe to stimulate the nerve so that it fires.

The discussion above is merely provided for general background information and is not intended to be used as an aid in determining the scope of the claimed subject matter. The claimed subject matter is not limited to implementations that solve any or all disadvantages noted in the background.

SUMMARY

A neuro-stimulation system includes a stimulator controller, a probe, and a magneto-ionic stimulator positioned on the probe and electrically connected to the stimulator controller. The stimulator controller can apply a voltage to the magneto-ionic stimulator, wherein a change in the voltage causes a change in a magnetic field produced by the magneto-ionic stimulator.

In accordance with a further embodiment, a method of stimulating a neuron includes placing a magneto-ionic stimulator near the neuron. A voltage applied to the magneto-ionic stimulator is changed to change the strength of a magnetic field generated by the magneto-ionic stimulator such that an electric field is generated along the neuron.

In accordance with a still further embodiment, a neuro-stimulation system includes a stimulator controller, a probe, and a magneto-ionic stimulator positioned on the probe and electrically connected to the stimulator controller. The magneto-ionic stimulator produces a magnetic field that oscillates at a frequency less than 10 Hz.

In accordance with some embodiments, the neuro-stimulation system includes a layer of $GdO_x$ in contact with a layer of Co. The stimulator controller applies a positive voltage across the $GdO_x$ layer to cause hydrogen to appear at the boundary between the $GdO_x$ layer and the Co layer. The magneto-ionic stimulator produces a weaker out-of-plane magnetic field when the hydrogen appears at the boundary. The stimulator controller removes the positive voltage across the $GdO_x$ layer to cause the hydrogen to move away from the boundary between the $GdO_x$ layer and the Co layer. The magneto-ionic stimulator produces a stronger out-of-plane magnetic field when the hydrogen moves away from the boundary.

In accordance with a further embodiment, the stimulator controller applies a negative voltage across the $GdO_x$ layer to drive oxygen into the Co layer. The magneto-ionic stimulator produces a weaker out-of-plane magnetic field when the oxygen is driven into the Co layer. The stimulator controller applies a positive voltage across the $GdO_x$ layer to drive oxygen out of the Co layer. The magneto-ionic stimulator produces a stronger out-of-plane magnetic field when the oxygen is driven out of the Co layer.

In accordance with a further embodiment, the magneto-ionic stimulator includes a layer of $GdO_x$ in contact with a layer of Pd, which is in contact with a layer of Co. The stimulator controller applies a positive voltage across the $GdO_x$ layer to drive hydrogen into the Pd layer. The magneto-ionic stimulator produces a weaker out-of-plane magnetic field when the hydrogen is driven into the Pd layer. The stimulator controller applies a negative voltage across the $GdO_x$ layer to cause the hydrogen to move out of the Pd layer. The magneto-ionic stimulator produces a stronger out-of-plane magnetic field when the hydrogen moves out of the Pd layer.

In accordance with one embodiment, the magneto-ionic stimulator includes a layer of oxide in contact with a layer of $CoFe_x$ alloy. In accordance with another embodiment, the magneto-ionic stimulator includes a layer of $GdO_x$ in contact with a layer of Pd, which is in contact with a layer of Co. In accordance with another embodiment, the magneto-ionic stimulator includes a layer of CoFeB that is in contact with a layer of MgO. In a still further embodiment, the layer of MgO is further in contact with an oxide layer such as $SiO_x$.

In accordance with one embodiment, the strength of the magnetic field produced by the magneto-ionic stimulator is controlled by controlling an amount of hydrogen at a boundary between two materials.

In accordance with a further embodiment, a neuro-stimulation system includes a stimulator controller, a support surface, and a spin orbit torque vortex stimulator positioned on the support surface and electrically connected to the stimulator controller such that the stimulator controller can apply a current to the spin orbit torque vortex stimulator. A change in the current causes a core of a magnetic field vortex produced by the spin orbit torque vortex stimulator to precess.

In accordance with a further embodiment, a neuro-stimulation system includes a stimulator controller, a support surface, and a magneto-ionic stimulator positioned on the support surface and electrically connected to the stimulator controller such that the stimulator controller can apply a voltage to the magneto-ionic stimulator. The magneto-ionic stimulator is an electrolytic gel and a change in the voltage causes a change in a magnetic field produced by the gel.

In accordance with a further embodiment, a neuro-stimulation system includes an array of magneto-ionic stimulators positioned proximate neurologic tissue and a controller changing a voltage applied to the magneto-ionic stimulators so as to cause a change in a magnetic field produced by the array of magneto-ionic stimulators.

In accordance with a further embodiment, the neurostimulation system further includes a wireless power receiver that receives power from a wireless power transmitter.

In accordance with a further embodiment, a method of stimulating a portion of an interoception system in a living body includes placing a magneto-ionic stimulator near the portion of the interoception system and changing a voltage applied to the magneto-ionic stimulator to change the strength of a magnetic field generated by the magneto-ionic stimulator such that an electric field is generated along the portion of the interoception system.

In accordance with a further embodiment, a method of stimulating tissue proximate the spine of a living body includes placing a magneto-ionic stimulator near the tissue and changing a voltage applied to the magneto-ionic stimulator to change the strength of a magnetic field generated by the magneto-ionic stimulator such that an electric field is generated along the tissue.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Below, embodiments of a magnetic field tissue stimulator are described. Each of these embodiments relies on a change in the out-of-plane magnetization of a thin layer of material as ions move within the stimulator. By applying a voltage, the ions are moved causing a resulting change in the magnetic field. As a result, a voltage control signal can be used to modulate the magnetic flux density of the magnetic field above the tissue stimulator. This fluctuating magnetic field creates an electric field in the target tissue that can, for example, cause neurons to fire.

A significant advantage of the embodiments is the frequency at which the magnetic field oscillates. Many prior art spintronic nano-sized stimulators are limited to operating in the MHz to GHz range. However, neurons do not react to such high frequency oscillations. Instead, the optimum frequency for neurostimulation is on the order of 1 Hz. The embodiments described below modulate the magnetic field at between 0.5-7.0 Hz thereby making them more effective spintronic neurostimulators.

Figure 1:
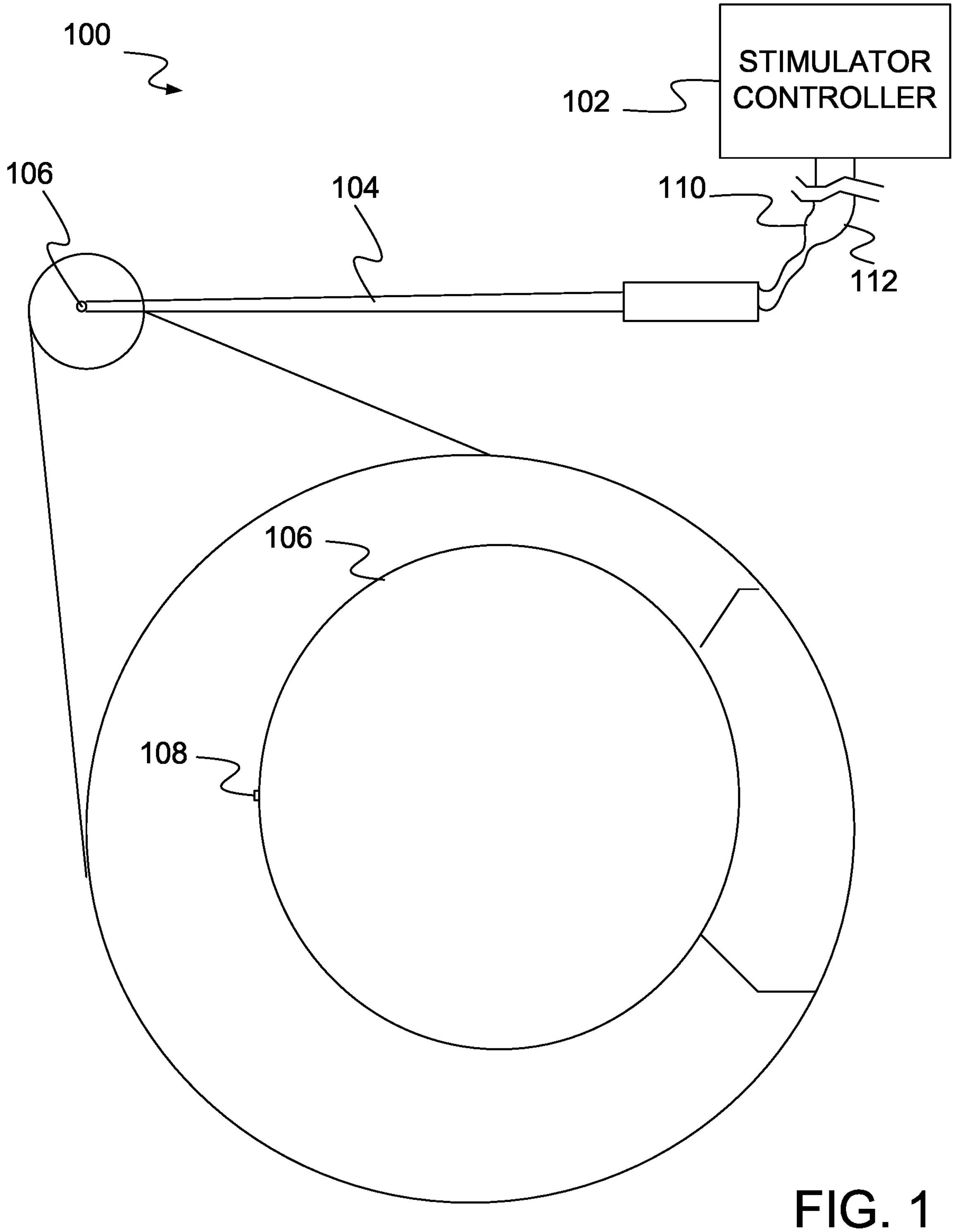
FIG. 1 is a schematic diagram of a neuro-stimulation system.

FIG. 1 provides a neurostimulation system 100 that includes a stimulator controller 102, a probe 104 having a support surface 106 and a magneto-ionic stimulator 108 located on support surface 106. Support surface 106 has a diameter on the order of 1 mm while magneto-ionic stimulator 108 has a width on the order of 10 micrometers. Conductors 110 and 112 provide an electrical connection between stimulator controller 102 and magneto-ionic stimulator 108 that allow stimulator controller 102 to apply different voltages to magneto-ionic stimulator so as to change the out-of-plane magnetic field produced by magneto-ionic stimulator 108.

Figure 2:
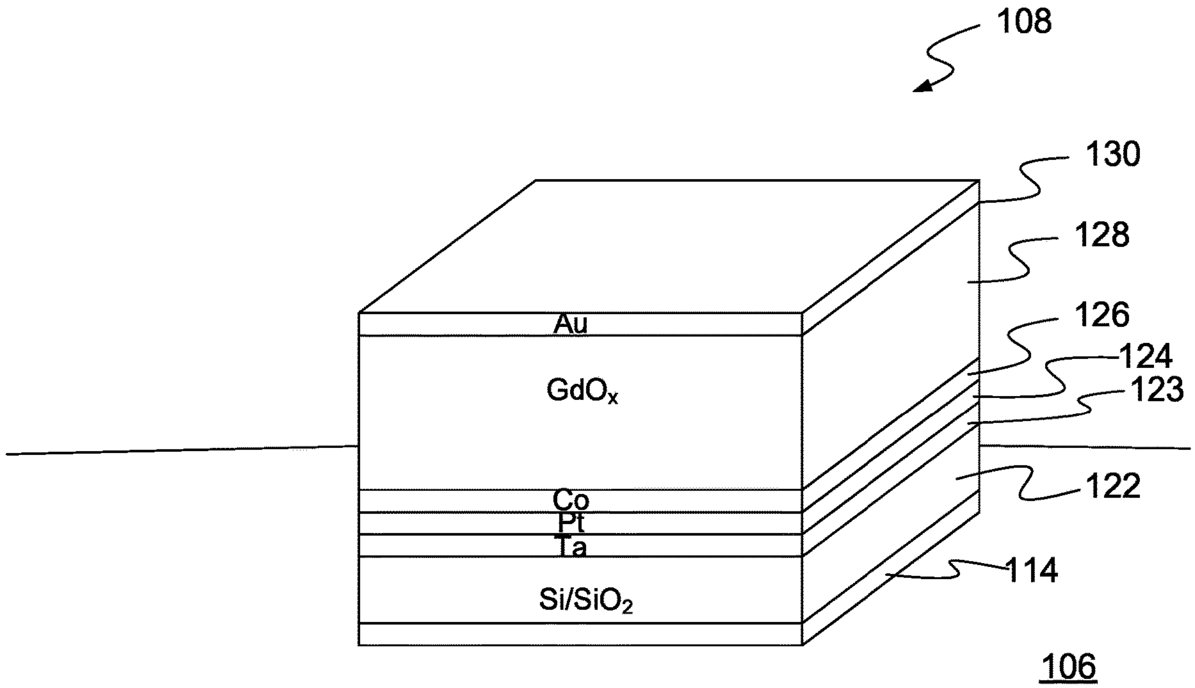
FIG. 2 is a perspective view of a probe and magneto-ionic stimulator in accordance with one embodiment.
Figure 3:
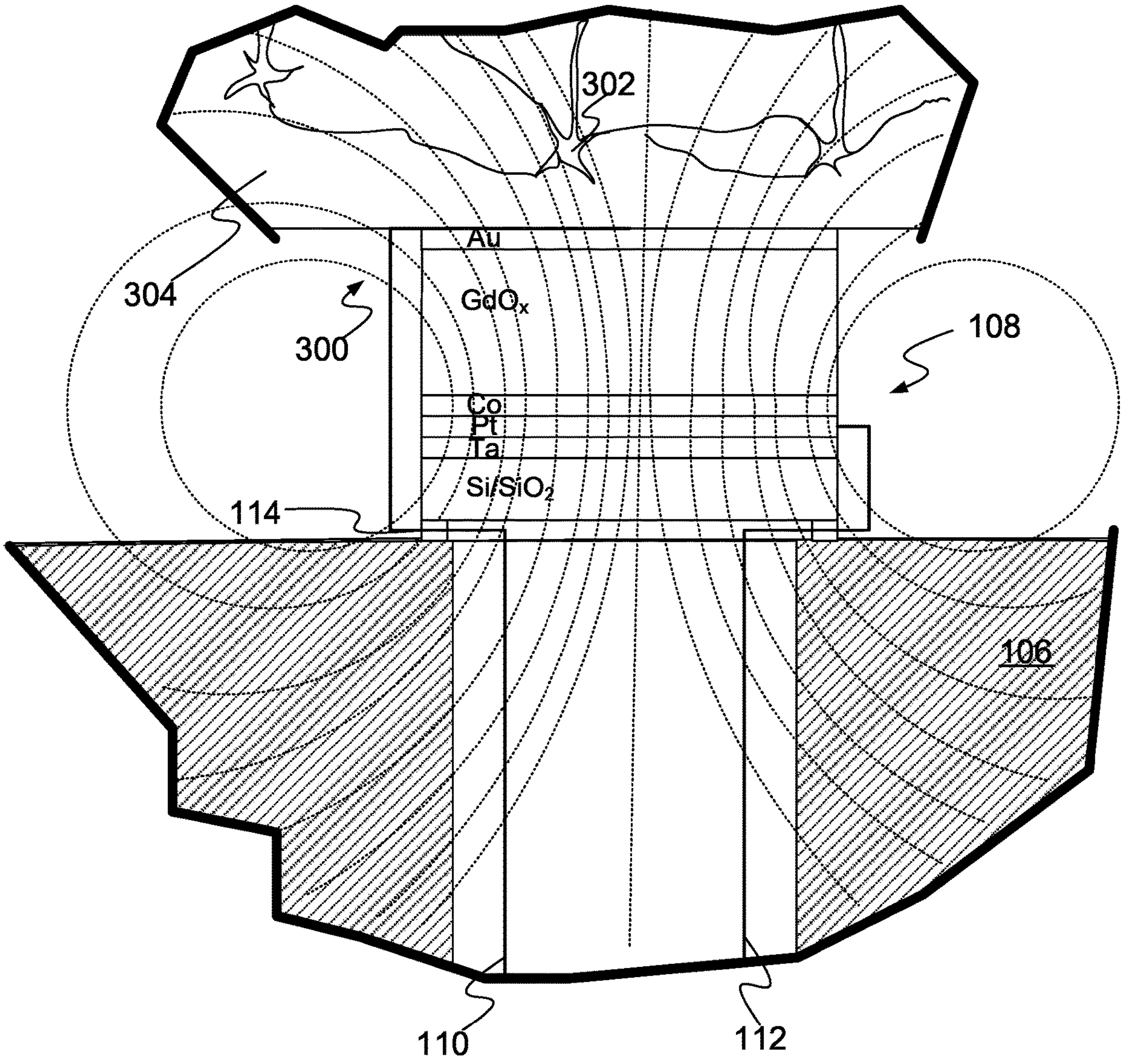
FIG. 3 is a side sectional view of the probe and magneto-ionic stimulator of FIG. 2 with the magneto-ionic stimulator in a first state.
Figure 4:
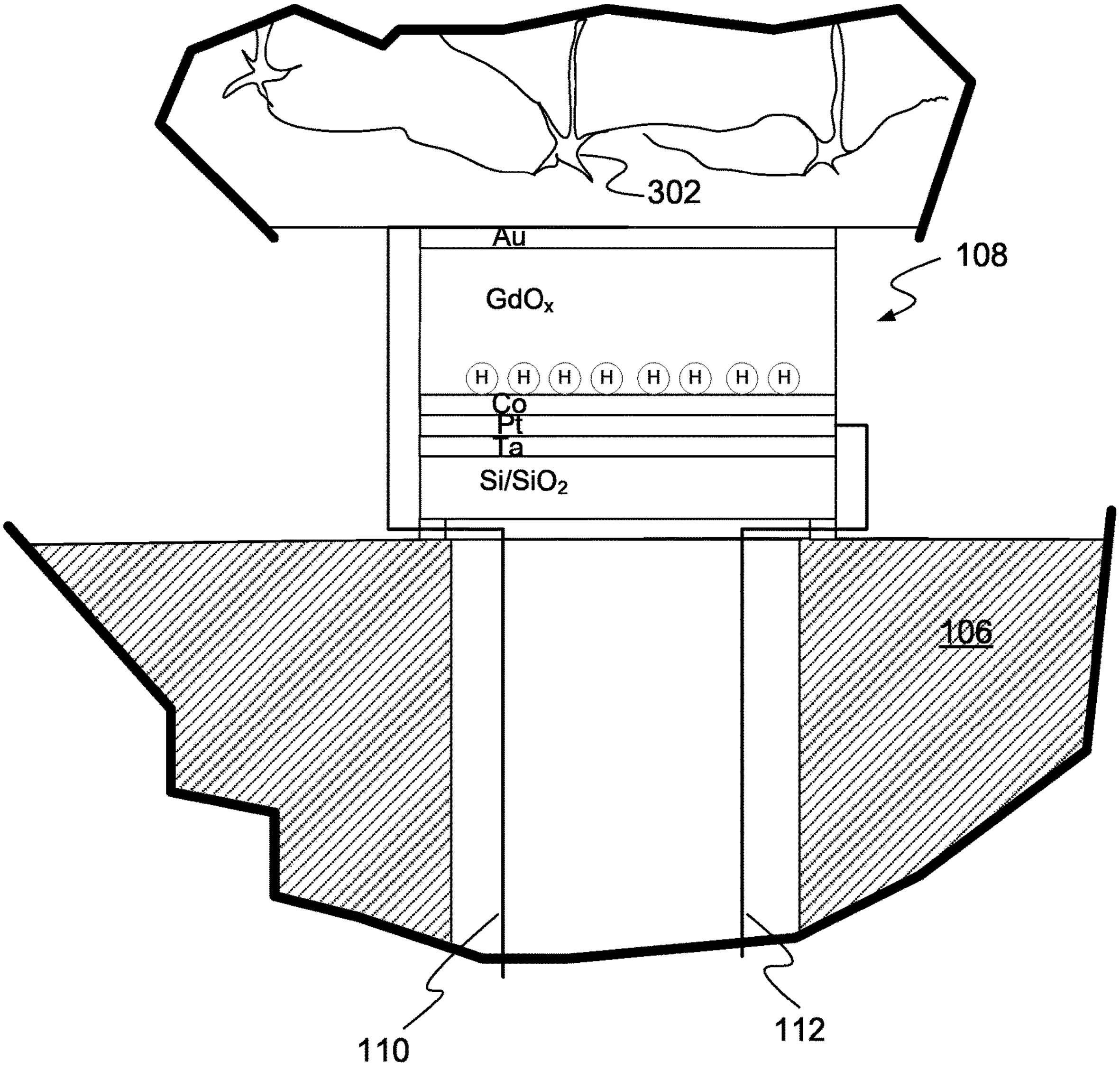
FIG. 4 is a side sectional view of the probe and magneto-ionic stimulator of FIG. 2 with the magneto-ionic stimulator in a second state.

FIG. 2 provides a perspective view of support surface 106 and stimulator 108. FIGS. 3 and 4 show side sectional views of support surface 106 and stimulator 108.

Stimulator 108 has a top surface pointing away from support surface 106 and a bottom surface facing support surface 106. The bottom surface of stimulator 108 is mounted on support surface 106 with an adhesive bead layer 114 between stimulator 108 and support surface 106. Adhesive bead layer 114 follows the perimeter of the bottom surface of stimulator 108 such that portions of the bottom surface remain exposed to support surface 106.

A layer 123 of Tantalum (Ta) is deposited on the top of a $Si/SiO_2$ substrate 122. A layer 124 of platinum (Pt) is deposited on layer 123. In accordance with one embodiment, Pt layer 124 has a height of 3 nm. Pt layer 124 is connected to conductor 112. A layer 126 of cobalt (Co) is deposited on top of Pt layer 124. In accordance with one embodiment, Co layer 126 has a height of 0.9 nm. A layer 128 of gadolinium oxide ($GdO_x$) is deposited on top of Co layer 126. In accordance with one embodiment, $GdO_x$ layer 128 has a height of 30 nm. A layer 130 of gold (Au) is deposited on top of $GdO_x$ layer 128. In accordance with one embodiment, Au layer 130 has a height of 3 nm. Au layer 130 is connected to conductor 110.

In FIG. 3, stimulator controller 102 has placed conductors 110 and 112 at the same voltage so that there is no voltage between Au layer 130 and Pt layer 124. In this state, Co layer 126 produces a magnetic field 300 (shown in dotted lines in FIG. 3) that extends perpendicularly out of the top surface of Co layer 126 and interacts with neurons, such as neuron 302 in tissue 304 that Au layer 130 is pressed against.

In FIG. 4, stimulator controller 102 has applied a positive voltage between conductors 110 and 112 creating a corresponding positive voltage between Au layer 130 and Pt layer 124. This positive voltage causes a layer of hydrogen to form at the interface between $GdO_x$ layer 128 and Co layer 126. This layer of hydrogen causes the magnetic field produced by Co layer 126 to rotate in plane thereby causing the magnetic field perpendicular to the top surface of Co layer 126 to disappear. As a result, there is no magnetic field passing through neuron 302.

In order to stimulate neuron 302, stimulator controller 102 applies positive voltage pulses on conductor 110 and connects conductor 112 to ground. Each voltage pulse creates a changing magnetic field that produces a corresponding electric field in neuron 302. A rising edge in the voltage creates a corresponding falling edge in the magnetic field. In accordance with one embodiment, the switching time between the rising edge in voltage and the falling edge in the magnetic field is 100 ms. Similarly, a falling edge in the voltage creates a corresponding rising edge in the magnetic field. In accordance with one embodiment, the switching time between falling edge in the voltage and the rising edge in the magnetic field is 400 ms. The difference between the switching times is due to the fact that when a positive voltage is applied to conductor 110, the voltage drives electrons into Pt layer 124 to facilitate the formation of the hydrogen layer. However, when conductor 110 is returned to ground, there is only a small electromotive force to draw electrons away from Pt layer 124 that will allow the hydrogen to move away from the interface.

Figure 6:
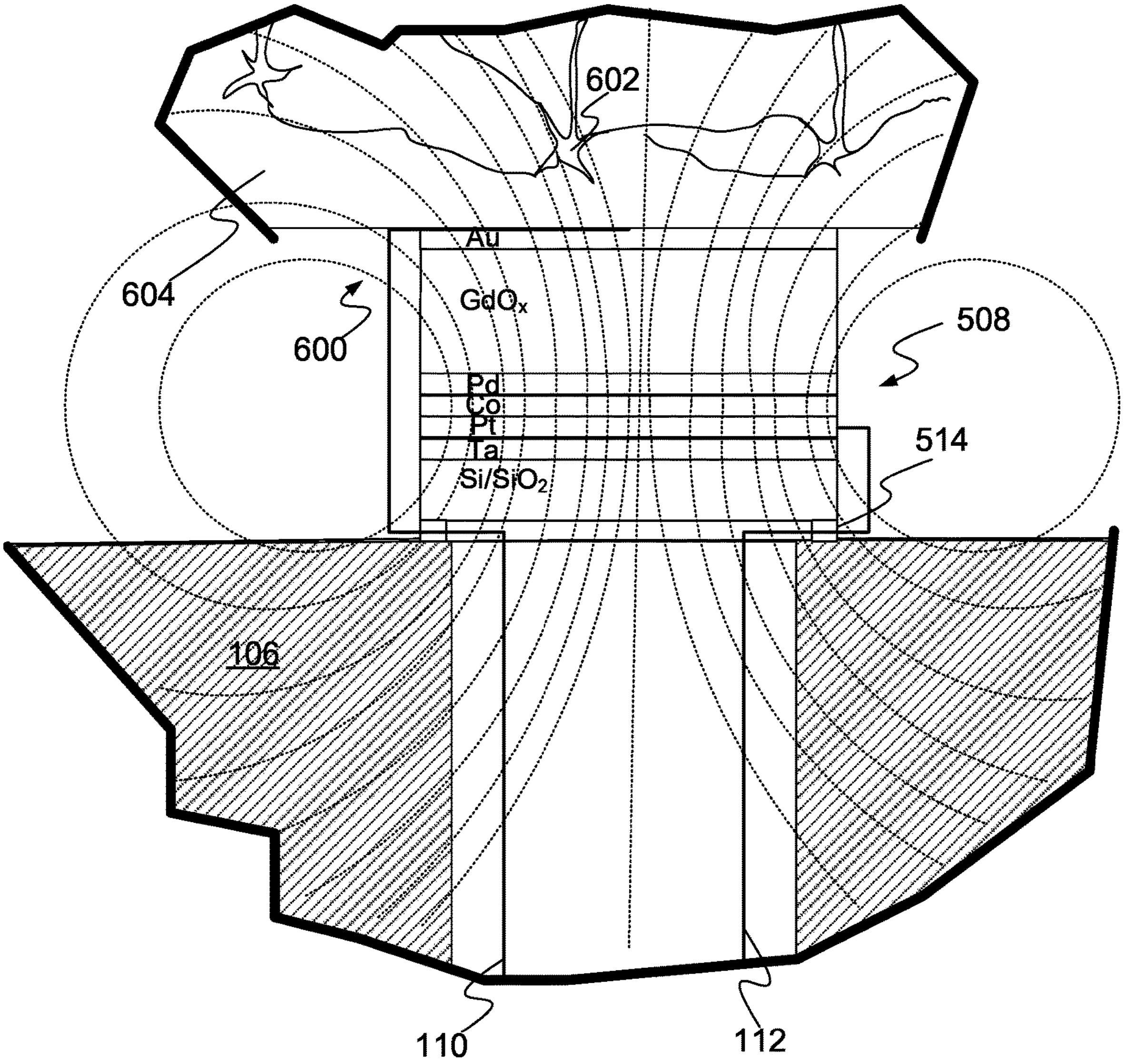
FIG. 6 is a side sectional view of the probe and magneto-ionic stimulator of FIG. 5 with the magneto-ionic stimulator in a first state.
Figure 7:
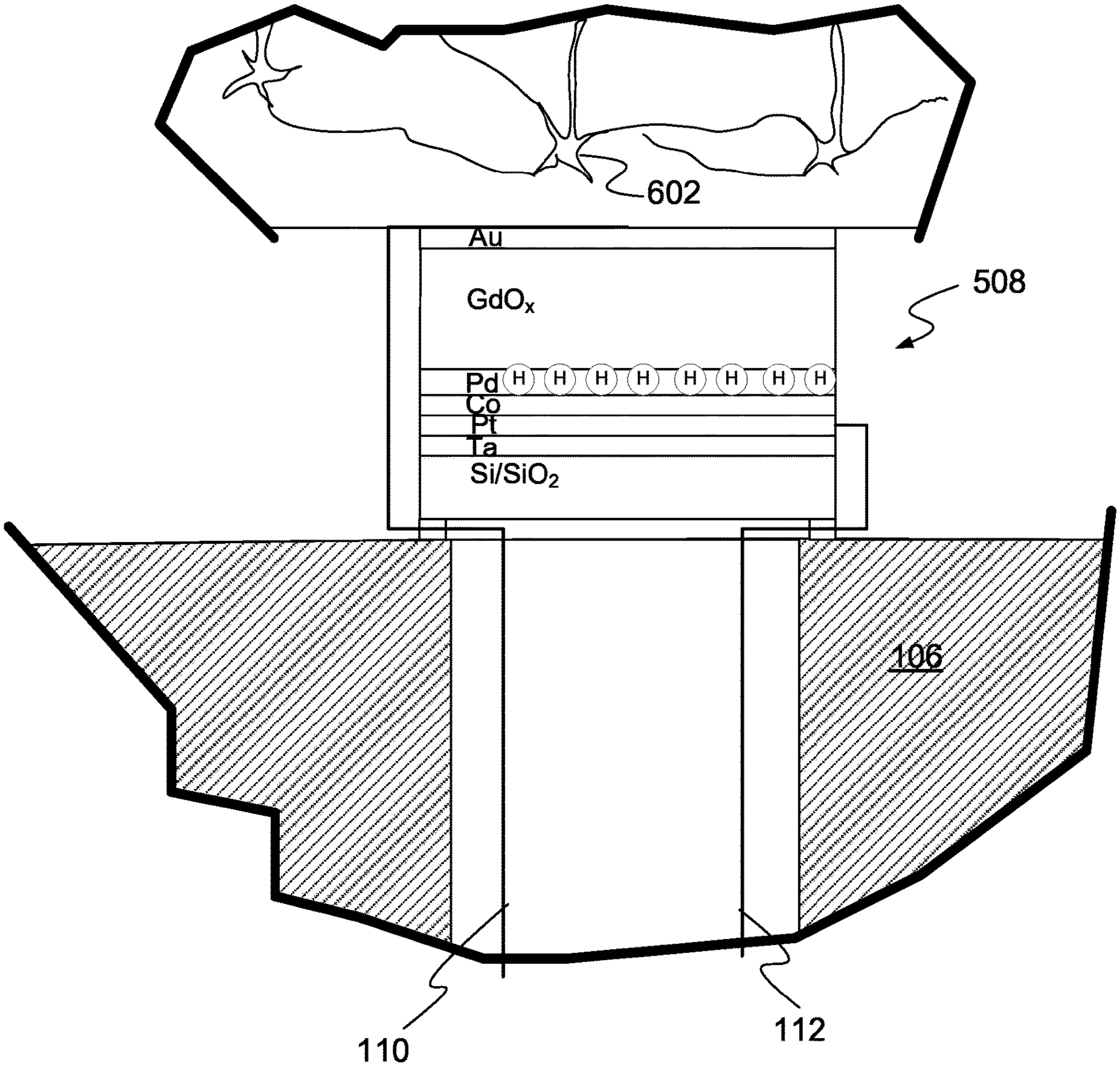
FIG. 7 is a side sectional view of the probe and magneto-ionic stimulator of FIG. 5 with the magneto-ionic stimulator in a second state.

In order to reduce the switching time for increasing the magnetic field, a negative voltage can be applied to conductor 110. However, applying a negative voltage on conductor 110 will cause oxygen to move into Co layer 126, which reduces the magnetic field instead of increasing the magnetic field. To avoid such oxidation of Co layer 126, a second embodiment of the stimulator, magneto-ionic stimulator 508, is provided as shown in FIGS. 5-7.

Figure 5:
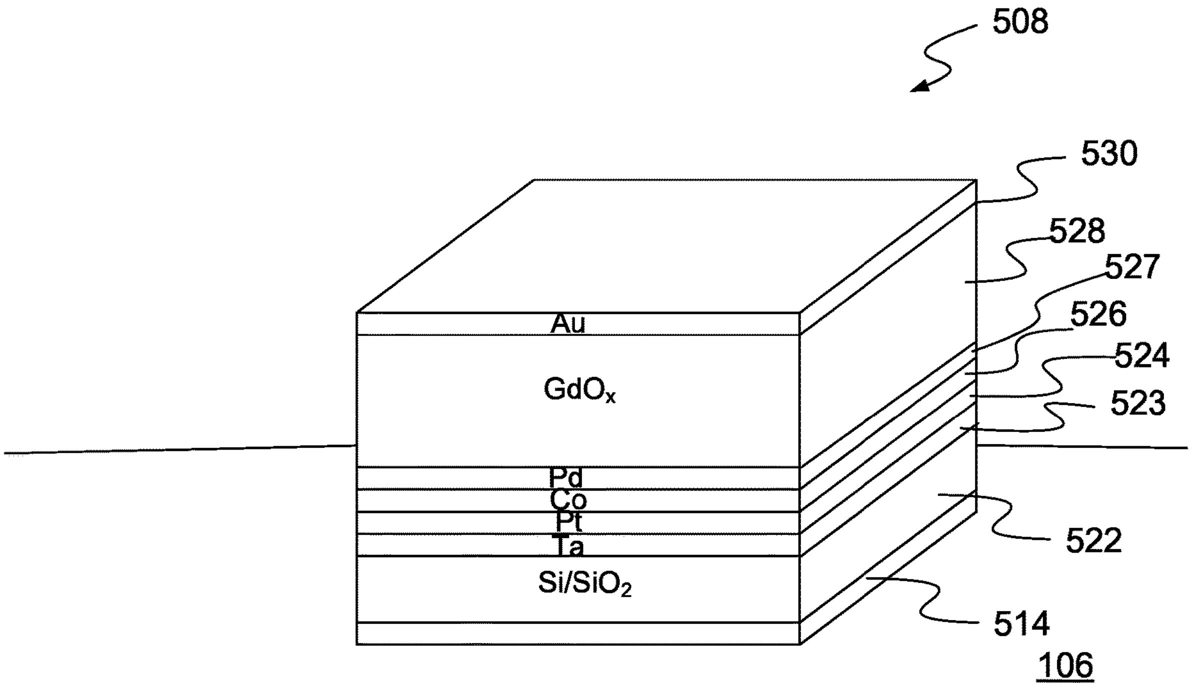
FIG. 5 is a perspective view of a probe and magneto-ionic stimulator in accordance with a second embodiment.

FIG. 5 provides a perspective view of stimulator 508 mounted on support surface 106. FIGS. 6 and 7 show side sectional views of support surface 106 and stimulator 508.

Stimulator 508 has a top surface pointing away from support surface 106 and a bottom surface facing support surface 106. The bottom surface of stimulator 508 is mounted on support surface 106 with an adhesive bead layer 514 between stimulator 508 and support surface 106. Adhesive bead layer 514 follows the perimeter of the bottom surface of stimulator 508 such that portions of the bottom surface remain exposed to support surface 106.

A layer 523 of Tantalum (Ta) is deposited on the top of a $Si/SiO_2$ substrate 522. A layer 524 of platinum (Pt) is deposited on layer 523. In accordance with one embodiment, Pt layer 524 has a height of 3 nm. Pt layer 524 is connected to conductor 112. A layer 526 of cobalt (Co) is deposited on top of Pt layer 524. In accordance with one embodiment, Co layer 526 has a height of 0.9 nm. A layer 527 of palladium (Pd) is deposited on top of Co layer 526. In accordance with one embodiment, Pd layer 527 has a height of 4.5 nm. A layer 528 of gadolinium oxide ($GdO_x$) is deposited on top of Pd layer 527. In accordance with one embodiment, $GdO_x$ layer 528 has a height of 30 nm. A layer 530 of gold (Au) is deposited on top of $GdO_x$ layer 528. In accordance with one embodiment, Au layer 530 has a height of 3 nm. Au layer 530 is connected to conductor 110.

In FIG. 6, stimulator controller 102 has placed a negative voltage on conductor 110 while keeping conductor 112 at ground so that there is negative voltage between Au layer 530 and Pt layer 524. In this state, Co layer 526 produces a magnetic field 600 (shown in dotted lines in FIG. 6) that extends perpendicularly out of the top surface of Co layer 526 and interacts with neurons, such as neuron 602 in tissue 604 that Au layer 530 is pressed against.

In FIG. 7, stimulator controller 102 has applied a positive voltage on conductor 110 creating a corresponding positive voltage between Au layer 530 and Pt layer 524. This positive voltage causes a layer of hydrogen to form at the interface between $GdO_x$ layer 528 and Co layer 526. This layer of hydrogen causes the magnetic field produced by Co layer 526 to rotate in plane thereby causing the magnetic field perpendicular to the top surface of Co layer 526 to disappear. As a result, there is no magnetic field passing through neuron 602.

In order to stimulate neuron 602, stimulator controller 102 alternates between providing positive and negative voltage pulses on conductor 110 and connects conductor 112 to ground. The alternating voltage pulses create a changing magnetic field that produces a corresponding electric field in neuron 602.

The addition of Pd layer 527 in the embodiment of FIGS. 5-7, protects Co layer 526 from oxidizing when a negative voltage is applied. During a positive voltage, hydrogen moves into Pd Layer 527 so that it still accumulates at the surface of Co layer 526. During a negative voltage pulse, electrons are pulled away from Pt layer 524 causing the hydrogen atoms to become $H^+$ protons that are then transported through $GdO_x$ layer 528 while Pd layer 527 prevents oxygen from reaching Co layer 526.

Figure 8:
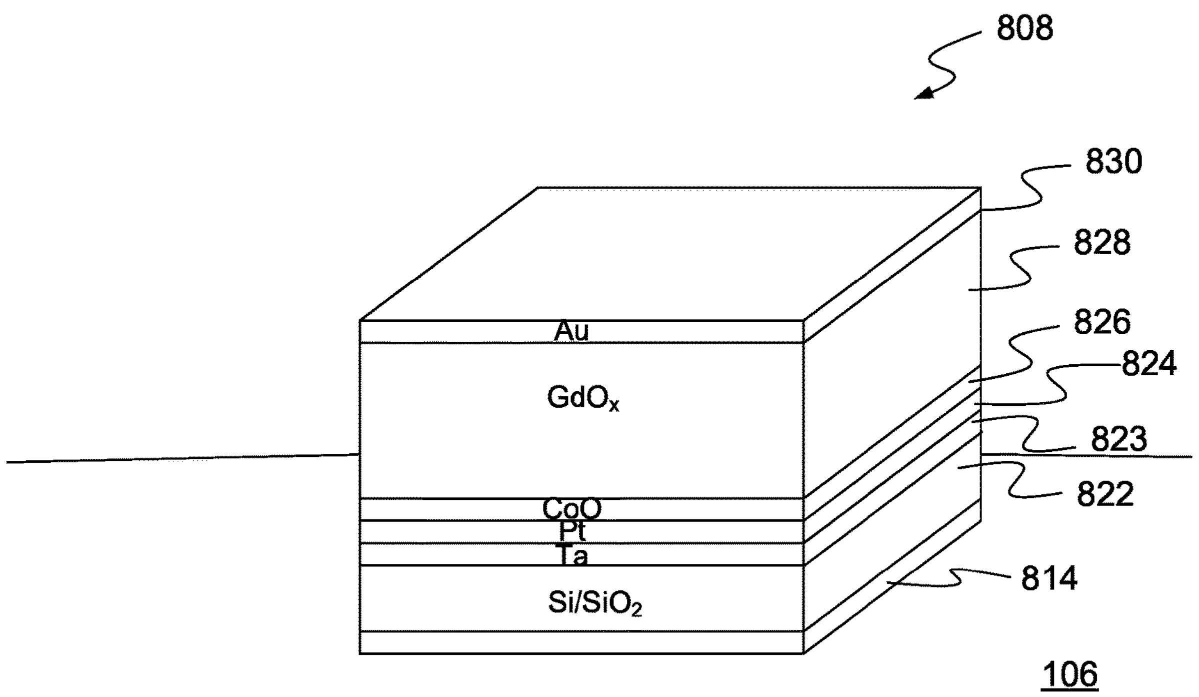
FIG. 8 is a perspective view of a probe and magneto-ionic stimulator in accordance with a third embodiment.
Figure 9:
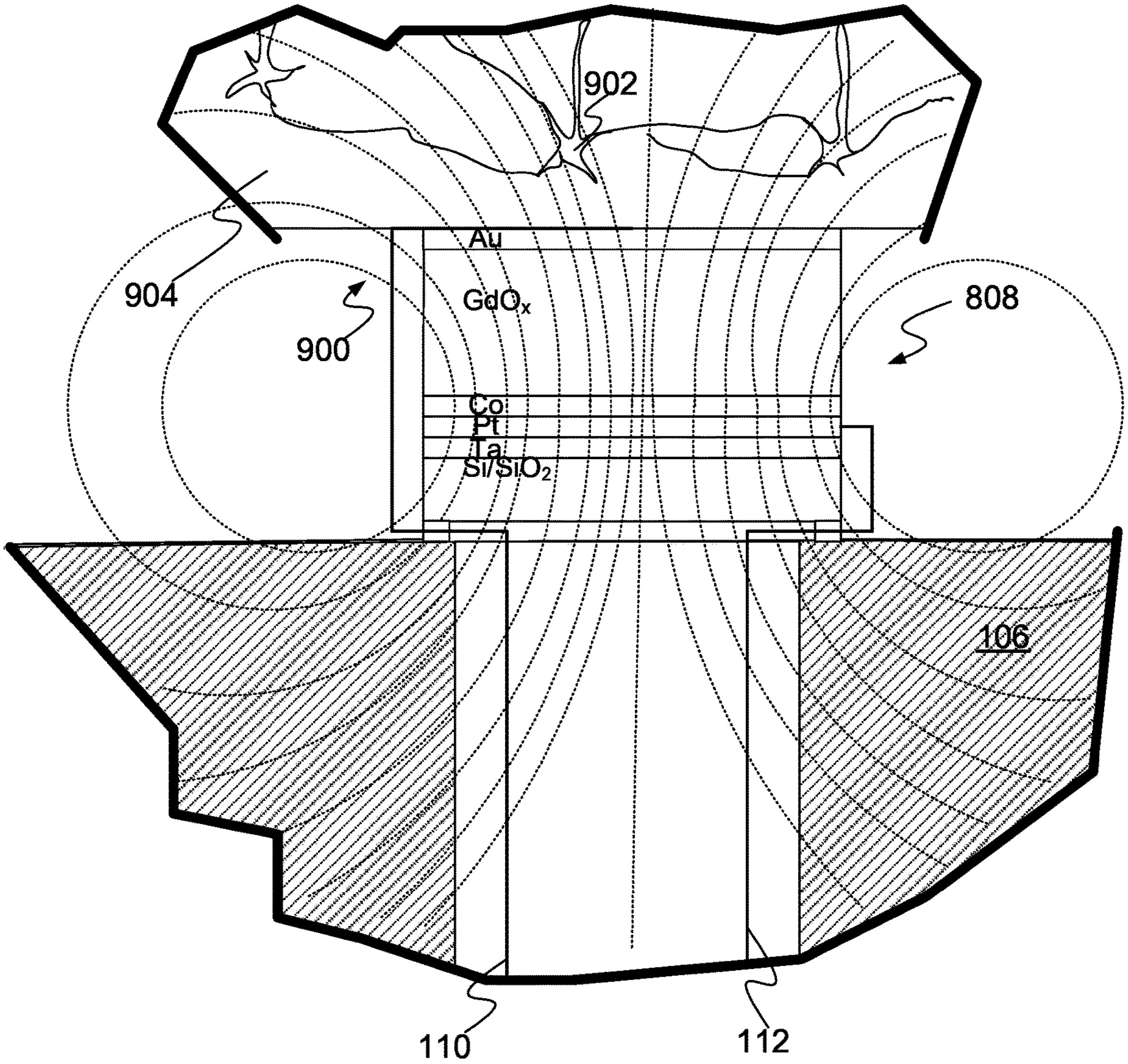
FIG. 9 is a side sectional view of the probe and magneto-ionic stimulator of FIG. 8 with the magneto-ionic stimulator in a first state.
Figure 10:
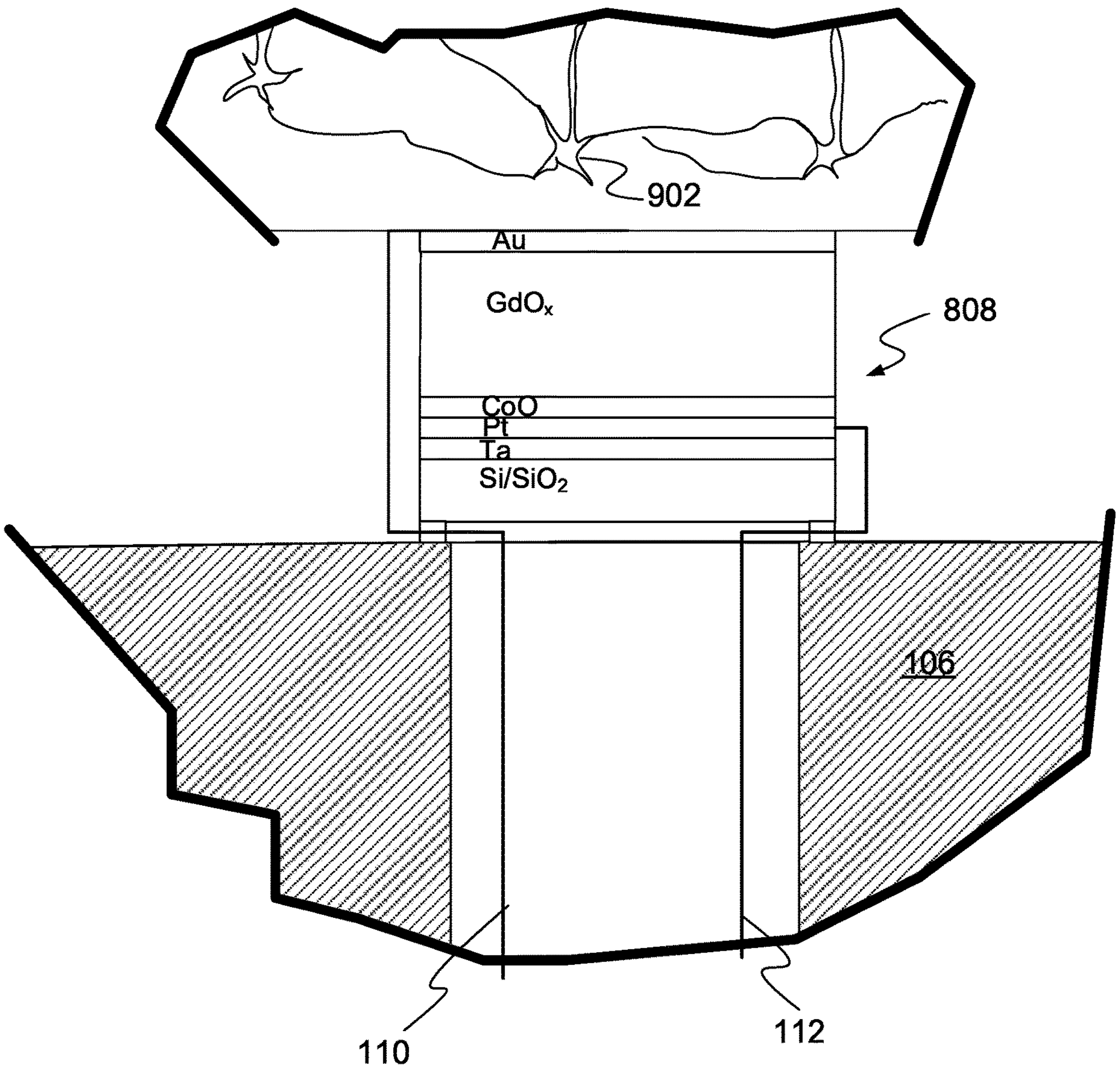
FIG. 10 is a side sectional view of the probe and magneto-ionic stimulator of FIG. 8 with the magneto-ionic stimulator in a second state.

FIG. 8 provides a perspective view of support surface 106 and a magneto-ionic stimulator 808 of a third embodiment. FIGS. 9 and 10 show side sectional views of support surface 106 and stimulator 808.

Stimulator 808 has a top surface pointing away from support surface 106 and a bottom surface facing support surface 106. The bottom surface of stimulator 808 is mounted on support surface 106 with an adhesive bead layer 814 between stimulator 808 and support surface 106. Adhesive bead layer 814 follows the perimeter of the bottom surface of stimulator 808 such that portions of the bottom surface remain exposed to support surface 106.

A layer 823 of Tantalum (Ta) is deposited on the top of a $Si/SiO_2$ substrate 822. A layer 824 of platinum (Pt) is deposited on layer 823. In accordance with one embodiment, Pt layer 824 has a height of 3 nm. Pt layer 824 is connected to conductor 112. A layer of cobalt (Co) is deposited on top of Pt layer 824. In accordance with one embodiment, the Co layer has a height of 0.9 nm. A layer 828 of Gadolinium oxide ($GdO_x$) is deposited on top of the Co layer. In accordance with one embodiment, $GdO_x$ layer 828 has a height of 30 nm. A layer 830 of gold (Au) is deposited on top of $GdO_x$ layer 828. In accordance with one embodiment, Au layer 830 has a height of 3 nm. Au layer 830 is connected to conductor 110.

Once constructed, a negative voltage is applied to conductor 110 to create a negative voltage between Au layer 830 and Pt layer 824. This negative voltage causes oxygen to be forced into the surface of the Co layer thereby forming a CoO layer 826. The negative voltage is then removed, leaving the oxygen in CoO layer 826.

In FIG. 9, stimulator controller 102 has applied a positive voltage to conductor 110 to create a positive voltage between Au layer 830 and Pt layer 824. In this state, the oxygen in CoO layer 826 is driven out of the layer producing a Co layer that generates a magnetic field 900 (shown in dotted lines in FIG. 9) that extends perpendicularly out of the top surface of the Co layer and interacts with neurons, such as neuron 902 in tissue 904 that Au layer 830 is pressed against.

In FIG. 10, stimulator controller 102 has applied a negative voltage between conductors 110 and 112 creating a corresponding negative voltage between Au layer 830 and Pt layer 824. This negative voltage drives oxygen back into the Co layer to reform CoO layer 826. The oxygen causes the magnetic field to rotate into the plane of the CoO layer 826 so that the magnetic field perpendicular to the top surface of CoO layer 826 disappears. As a result, there is no magnetic field passing through neuron 902.

In order to stimulate neuron 902, stimulator controller 102 alternates between applying a positive voltage and a negative voltage on conductor 110 and connects conductor 112 to ground. Each voltage pulse creates a changing magnetic field that produces a corresponding electric field in neuron 902.

Figure 11:
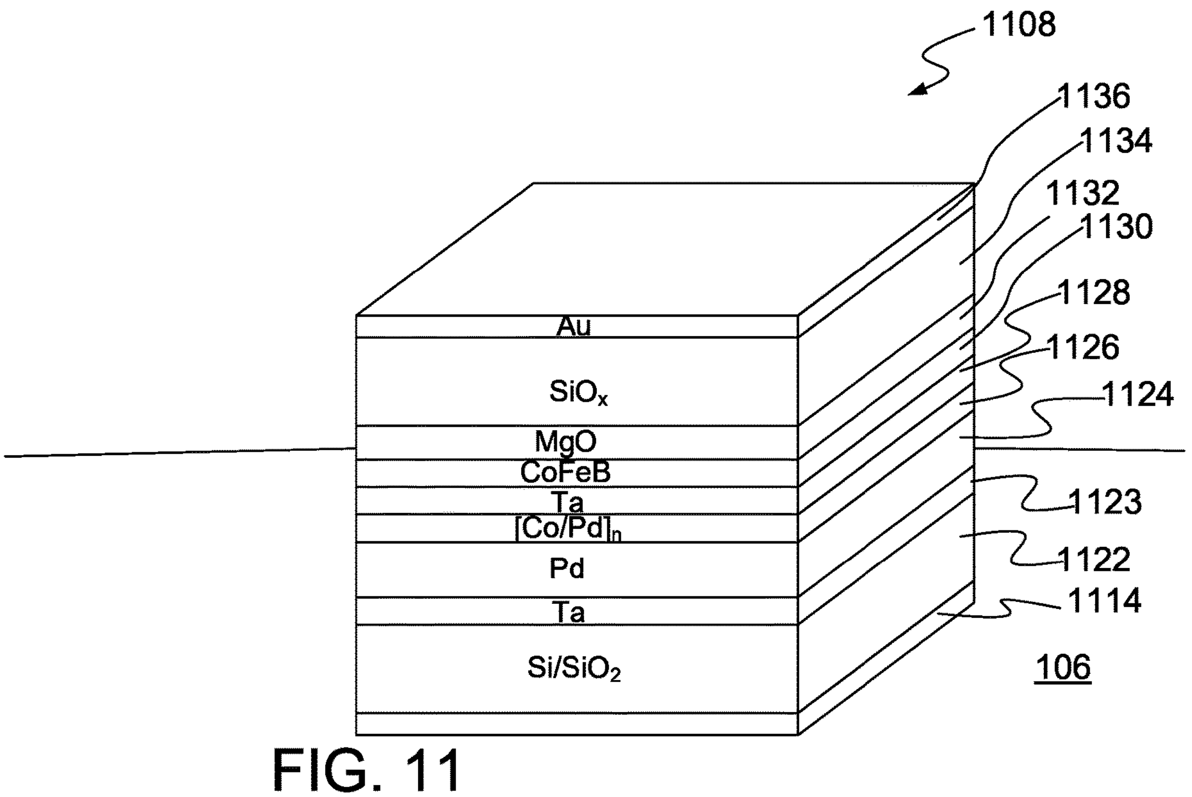
FIG. 11 is a perspective view of a probe and magneto-ionic stimulator in accordance with a fourth embodiment.
Figure 12:
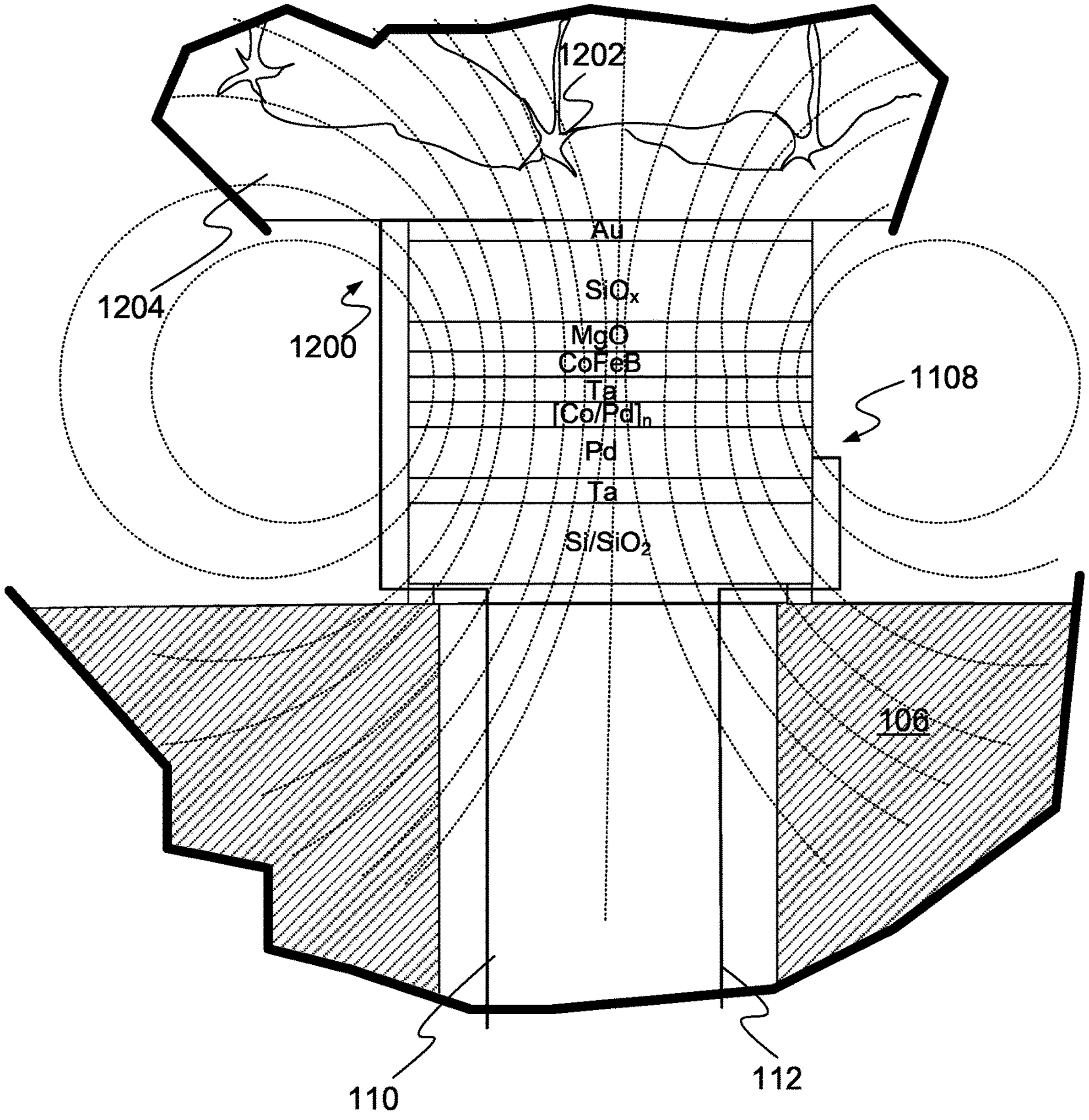
FIG. 12 is a side sectional view of the probe and magneto-ionic stimulator of FIG. 11 with the magneto-ionic stimulator in a first state.
Figure 13:
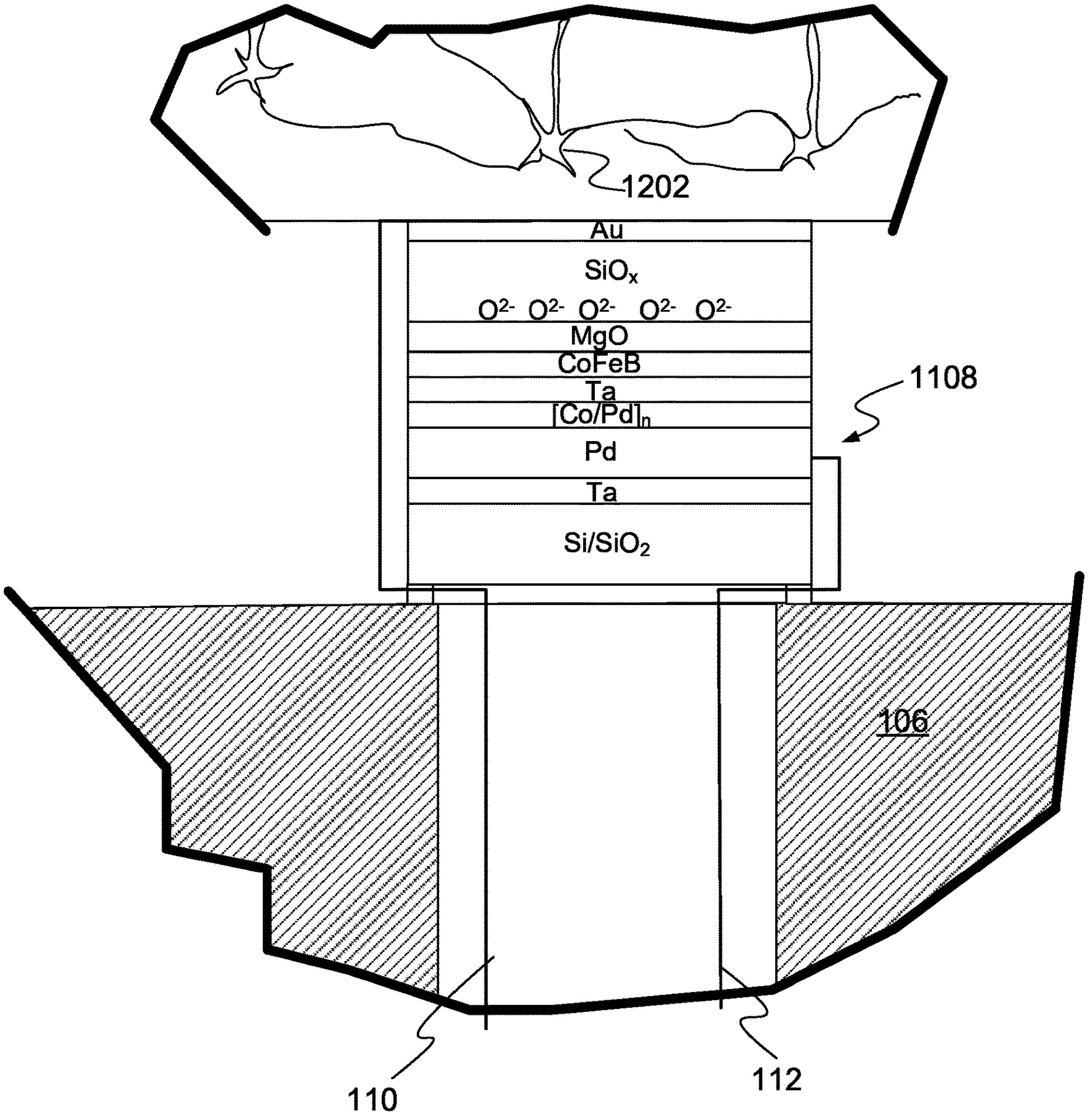
FIG. 13 is a side sectional view of the probe and magneto-ionic stimulator of FIG. 12 with the magneto-ionic stimulator in a second state.

FIG. 11 provides a perspective view of support surface 106 and a magneto-ionic stimulator 1108 of a fourth embodiment. FIGS. 12 and 13 show side sectional views of support surface 106 and stimulator 1108.

Stimulator 1108 has a top surface pointing away from support surface 106 and a bottom surface facing support surface 106. The bottom surface of stimulator 1108 is mounted on support surface 106 with an adhesive bead layer 1114 between stimulator 1108 and support surface 106. Adhesive bead layer 1114 follows the perimeter of the bottom surface of stimulator 1108 such that portions of the bottom surface remain exposed to support surface 106.

A layer 1123 of tantalum (Ta) is deposited on the top of a Si/$SiO_2$ substrate 1122. A layer 1124 of palladium (Pd) is deposited on layer 1123. In accordance with one embodiment, Pd layer 1124 has a height of 10 nm. Pd layer 1124 is connected to conductor 112. A layer 1126 consisting of multiple alternating layers of cobalt (Co) and palladium (Pd) is deposited on top of Pd layer 1124. In accordance with one embodiment, Co/Pd multilayer 1126 has a height of 3 nm. A layer 1128 of tantalum is deposited on top of Co/Pd multilayer 1126. In accordance with one embodiment, Ta layer 1128 has a height of 1 nm. A layer 1130 of CoFeB is deposited on top of tantalum layer 1128. In accordance with one embodiment, CoFeB layer 1130 has a height of 1.3 nm. A layer 1132 of MgO is deposited on CoFeB layer 1130. In accordance with one embodiment, MgO layer 1132 has a height of 2 nm. A layer 1134 of $SiO_x$ is deposited on MgO layer 1132. A layer 1136 of gold (Au) is deposited on top of $SiO_x$ layer 1134. In accordance with one embodiment, Au layer 1136 has a height of 3 nm. Au layer 1130 is connected to conductor 110.

In FIG. 12, stimulator controller 102 has applied a positive voltage to conductor 110 to create a positive voltage between Au layer 1136 and Pd layer 1124. In this state, ionic oxygen in $SiO_x$ layer 1134 is driven away from MgO layer 1132 thereby allowing CoFeB layer 1130 to generate a magnetic field 1200 (shown in dotted lines in FIG. 12) that extends perpendicularly out of the top surface of CoFeB layer 1130 and interacts with neurons, such as neuron 1202 in tissue 1204 that Au layer 1136 is pressed against.

In FIG. 13, stimulator controller 102 has applied a negative voltage between conductors 110 and 112 creating a corresponding negative voltage between Au layer 1136 and Pd layer 1124. This negative voltage drives ionic oxygen toward MgO layer 1132 thereby causing the magnetic field to rotate into the plane of the CoFeB layer 1130 so that the magnetic field perpendicular to the top surface of CoFeB layer 1130 disappears. As a result, there is no magnetic field passing through neuron 1202.

In order to stimulate neuron 1202, stimulator controller 102 alternates between applying a positive voltage and a negative voltage on conductor 110 and connects conductor 112 to ground. Each voltage pulse creates a changing magnetic field that produces a corresponding electric field in neuron 1102.

Each of the embodiments described above create a time-varying magnetic field has a frequency of oscillation that is limited by ionic transport speed. As a result, the switching provided by the embodiments is in the range of 0.5 Hz-100 kHz. This aligns well with the optimum frequency for stimulating neurons of ~100 Hz. As a result, the embodiments are well-suited for neuron stimulation.

Figure 14:
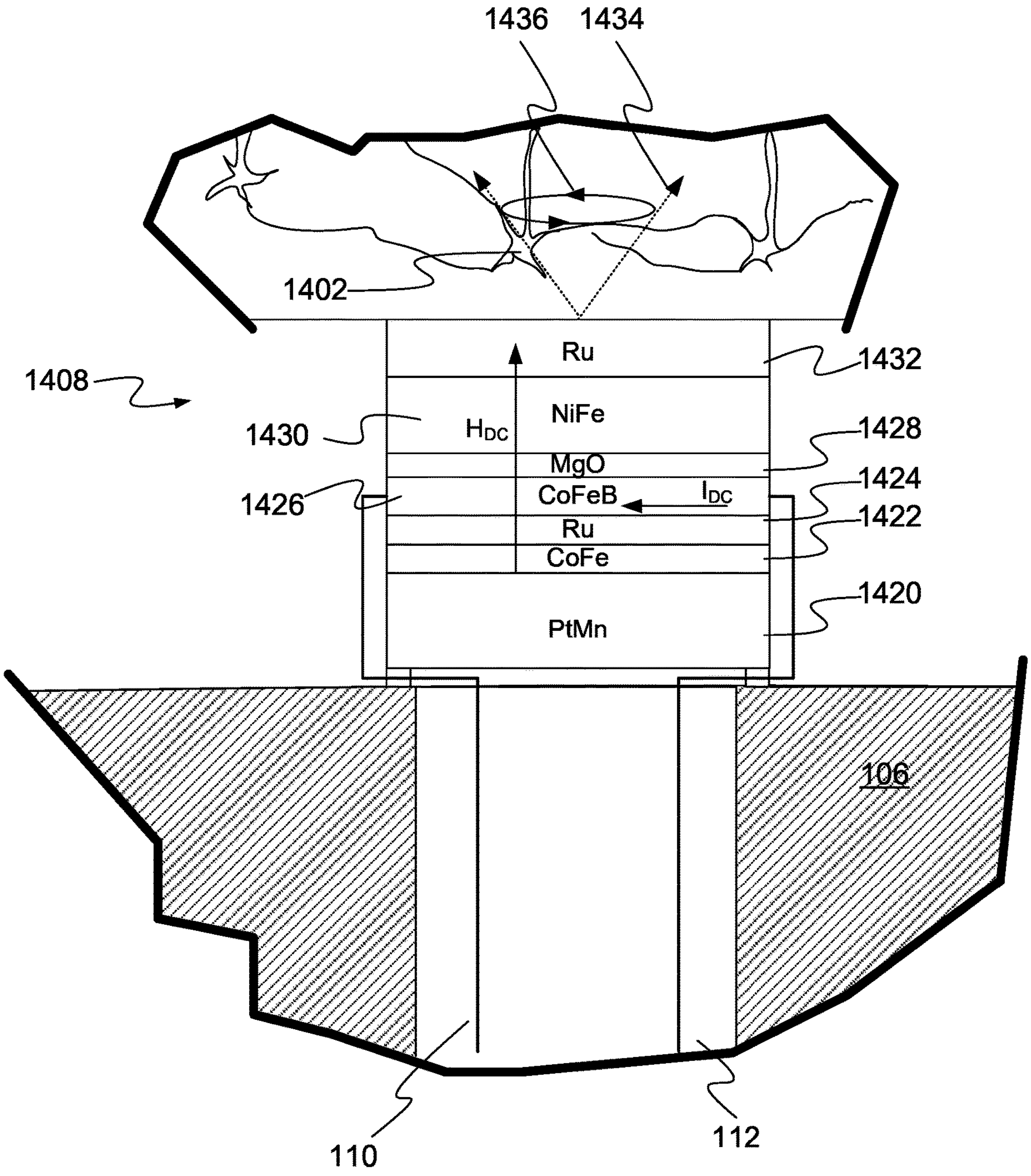
FIG. 14 provides a side sectional view of a neurostimulator at the end of a probe in accordance with a fifth embodiment.

FIG. 14 provides a side sectional view of a neurostimulator 1408 at the end of probe 106. Neurostimulator 1408 is a spin orbit torque vortex device, A bottom contact layer 1420 of neurostimulator 1408 is made of PtMn and has a height of 15 nm. A layer 1422 of CoFe is deposited on top of layer 1420 and has a height of 2.5 nm. A layer 1424 of Ru is deposited on layer 1422 and has a height of 0.85 nm. A layer 1426 of CoFeB is deposited on top of layer 1424 and has a height of 3 nm. Layer 1426 provides a fixed magnetic layer. A layer 1428 of MgO is deposited on top of layer 1426 and has a height of 1.075 nm. Layer 1428 acts as a barrier layer. A layer 1430 of NiFe is deposited on top of layer 1428 and has a height of 15 nm. Layer 1430 acts as a free layer. A cap layer 1432 of Ru is deposited on layer 1430 and has a height of 10 nm.

Neurostimulator 1408 uses a current $I_{dc}$ in the plane of layer 1426 and a magnetic field $H_{dc}$ that is perpendicular to the plane of layer 1426 to cause the core 1434 of a magnetic vortex within neurostimulator 1408 to precess 1436. This results in an oscillating magnetic field external to neurostimulator 1408 that induces an oscillating electric field that can cause neuron 1402 to fire. The oscillations have a frequency on the order of GHz with the actual frequency being set by the size of the current in layer 1426. This is a significant improvement over nanowire stimulation, which has a frequency between MHz and GHz. Neurostimulator 1408 also only requires 5 nW of power, which implies low thermal effects on tissue.

Figure 15:
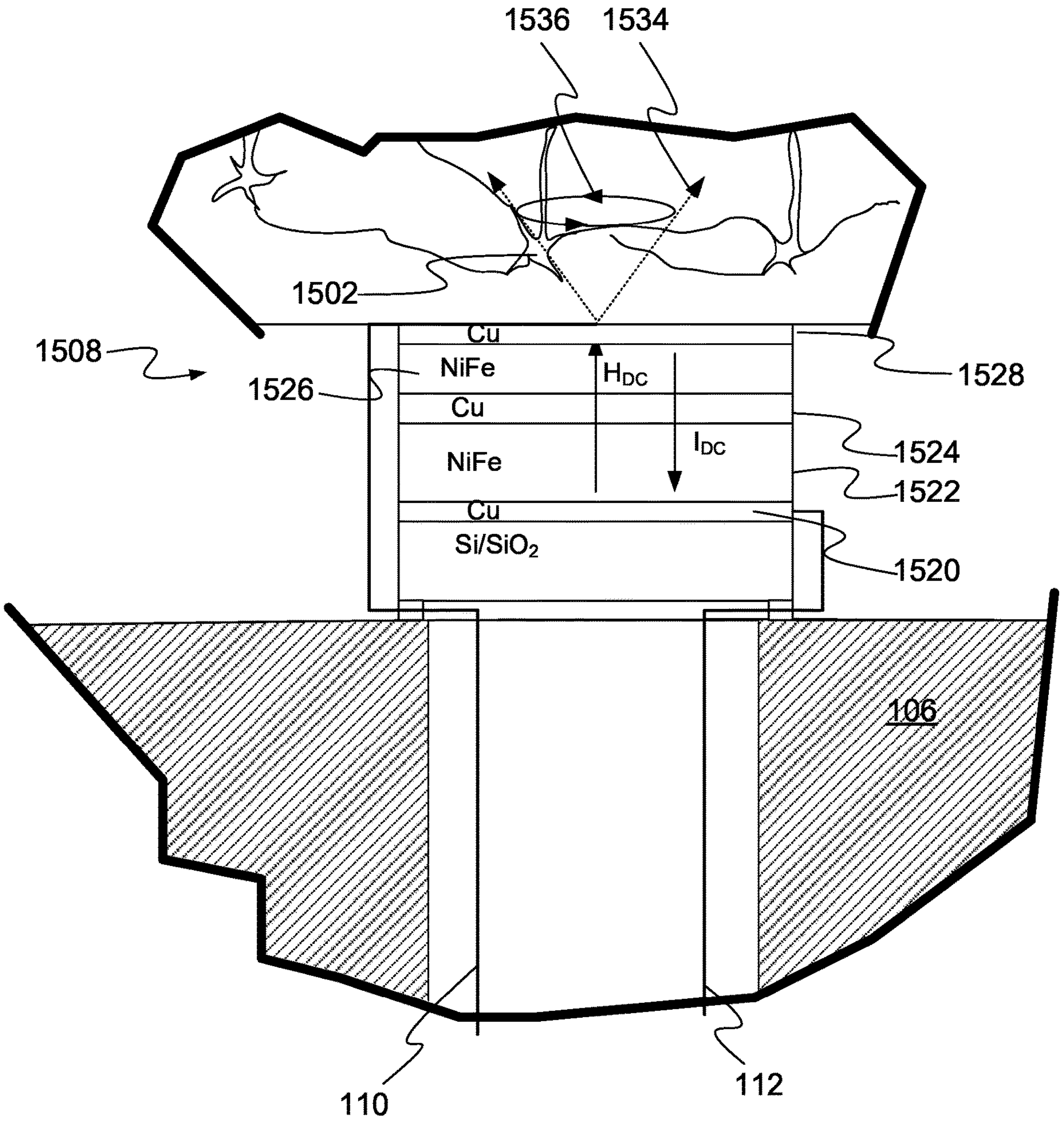
FIG. 15 provides a side sectional view of a neurostimulator at the end of a probe in accordance with a sixth embodiment.

FIG. 15 provides a side sectional view of a neurostimulator 1508 at the end of probe 106. Neurostimulator 1508 is a spin orbit torque vortex device. A bottom conductor layer 1520 of Cu has a layer 1522 of NiFe deposited on it. Layer 1522 provides a fixed magnetic layer. A thin layer 1524 of Cu is deposited on top of layer 1522 and acts as a barrier layer. A layer 1526 of NiFe is deposited on top of layer 1524 and acts as a free layer. A top conductor layer 1528 of Cu is deposited on layer 1526.

Neurostimulator 1508 uses a current $I_{dc}$ between top conductor layer 1528 and bottom conductor layer 1520 and a magnetic field $H_{dc}$ that is perpendicular to the plane of layer 1522 to cause the core 1534 of a magnetic vortex within neurostimulator 1508 to precess 1536. This results in an oscillating magnetic field external to neurostimulator 1508 that induces an oscillating electric field that can cause neuron 1502 to fire. The frequency of oscillation is on the order of 1.0 GHz.

Figure 16:
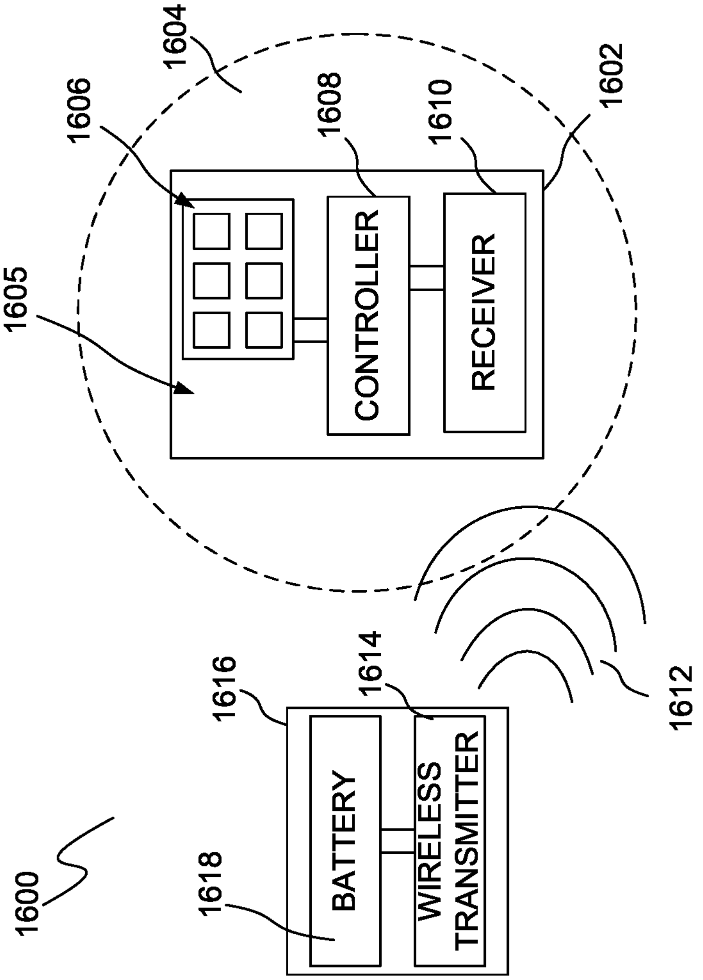
FIG. 16 provides schematic view of neurostimulator with an on-chip wireless power transfer system in accordance with a seventh embodiment.

FIG. 16 provides a schematic diagram of an alternative neurostimulation system 1600 that includes an implantable structure 1602 that can be surgically implanted within a living body 1604. Implantable structure 1602 includes an array 1606 of neurostimulators that are mounted on a support surface 1605 of structure 1602 and that are in contact with tissue in living body 1604 after implantation. The neurostimulators can be any of the magneto-ionic neurostimulators discussed above. Implantable structure 1602 also supports a controller 1608 and a wireless receiver 1610. Controller 1608 controls the application of voltage and/or current to the neurostimulators in array 1606 to thereby control the magnetic fields generated by the neurostimulators in array 1606. Wireless receiver 1610 receives a wireless signal 1612 generated by a wireless transmitter 1614 outside of living body 1604. Wireless signal 1612 generates a voltage in receiver 1610 that is then used to provide power to controller 1608. Controller 1608 uses this power to apply the voltage and/or current to the neurostimulators in array 1606. In accordance with one embodiment, wireless transmitter 1614 is contained within a mobile container 1616 that can be carried by the person implanted with structure 1602. Mobile container 1616 also includes a battery 1618, which provides power to wireless transmitter 1614.

Although the neurostimulators have been discussed above in connection with neurons in the brain, the neurostimulators may be used in other parts of the neurologic system, such as neurologic tissue in the spine. In accordance with some embodiments, the neurostimulators are used on tissue of the interoception system of the body.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. A neuro-stimulation system comprising:

a stimulator controller, a support surface configured to be positioned within a living body, and a magneto-ionic stimulator comprising planar layers positioned on the support surface, the planar layers comprising a planar layer of cobolt-iron-boron (CoFeB) that is in contact with a planar layer of magnesium oxide (MgO) and the planar layers electrically connected to the stimulator controller in a manner that the stimulator controller applies a voltage to the magneto-ionic stimulator, wherein a change in the voltage changes a magnetic flux density of an out-of-plane magnetic field produced by the magneto-ionic stimulator at a frequency between 0.5 Hz and 100 KHz, wherein the out-of-plane magnetic field is out-of-plane relative to the planar layers.

2. A method of stimulating a neuron comprising:

placing a magneto-ionic stimulator comprising a planar layer of cobolt-iron-boron (CoFeB) that is in contact with a planar layer of magnesium oxide (MgO) within a living body near the neuron; and using a controller connected to the stimulator to change a voltage applied to the magneto-ionic stimulator to change the strength of an out-of-plane magnetic field generated by the magneto-ionic stimulator at a frequency between 0.5 Hz and 100 KHz in a manner that an electric field is generated along the neuron, wherein the out-of-plane magnetic field is out-of-plane relative to the planar layers.

3. The method of claim 2, wherein the layer of MgO is further in contact with an oxide layer.

4. A neuro-stimulation system comprising:

a stimulator controller, a support surface, and a magneto-ionic stimulator positioned on the support surface and electrically connected to the stimulator controller, wherein the magneto-ionic stimulator comprises a planar layer of cobolt-iron-boron (CoFeB) that is in contact with a planar layer of magnesium oxide (MoO) and produces an out-of-plane magnetic field that oscillates at a frequency less than 10 kHz, wherein the out-of-plane magnetic field is out-of-plane relative to the planar layers.

* * * * *